United States Patent [19]

Yamaguchi et al.

[11] Patent Number: 5,214,282
[45] Date of Patent: May 25, 1993

[54] METHOD AND APPARATUS FOR PROCESSING A MINUTE PORTION OF A SPECIMEN

[75] Inventors: Hiroshi Yamaguchi, Fujisawa; Minori Noguchi, Yokohama; Makiko Kohno, Kawasaki; Toshihiko Nakata, Hiratsuka, all of Japan

[73] Assignee: Hitachi, Ltd., Tokyo, Japan

[21] Appl. No.: 707,774

[22] Filed: May 30, 1991

[30] Foreign Application Priority Data

May 30, 1990 [JP] Japan .................................. 2-138197
Sep. 28, 1990 [JP] Japan .................................. 2-256892

[51] Int. Cl.⁵ .......................................... H01J 37/26
[52] U.S. Cl. ...................................... 250/307; 250/306; 250/492.2
[58] Field of Search ............... 250/307, 306, 492.2 R, 250/492.21

[56] References Cited

U.S. PATENT DOCUMENTS 4,550,257 10/1985 Binnig et al. ..................... 250/492.2
4,921,346 5/1990 Tukomoto et al. ................ 250/306
4,983,540 1/1991 Yamaguchi et al. ............... 437/110

FOREIGN PATENT DOCUMENTS 0317952 5/1989 European Pat. Off. .
0376045 1/1990 European Pat. Off. .
352789 7/1990 European Pat. Off. .
9004753 5/1990 PCT Int'l Appl. .

OTHER PUBLICATIONS

U. Dürig et al. "Near-field optical-scanning microscopy", Journal of Applied Physics, vol. 59, No. 10, May 15, 1986, pp. 3318-3327.
H. Sakaki "Scattering Suppression and High-Mobility Effect of Size-Quantized Electrons in Ultrafine Semiconductor Wire Structures," Japanese Journal of Applied Physics, vol. 19, No. 12, Sep. 16, 1980, pp. L735-L738.
Yamaguchi et al. "Method and apparatus for processing a fine pattern" U.S. Patent Application Ser. No. 07/455,155.

Primary Examiner—Jack I. Berman
Assistant Examiner—Kiet T. Nguyen
Attorney, Agent, or Firm—Antonelli, Terry, Stout & Kraus

[57] ABSTRACT

An image of a specimen which is to be processed is detected by a near-field optical scanning microscope. An image with extremely high resolution for identifying a minute portion of several tens nm is detected. The detected minute portion is processed by, for example, a tunnel current of a scanning tunneling microscope.

69 Claims, 21 Drawing Sheets

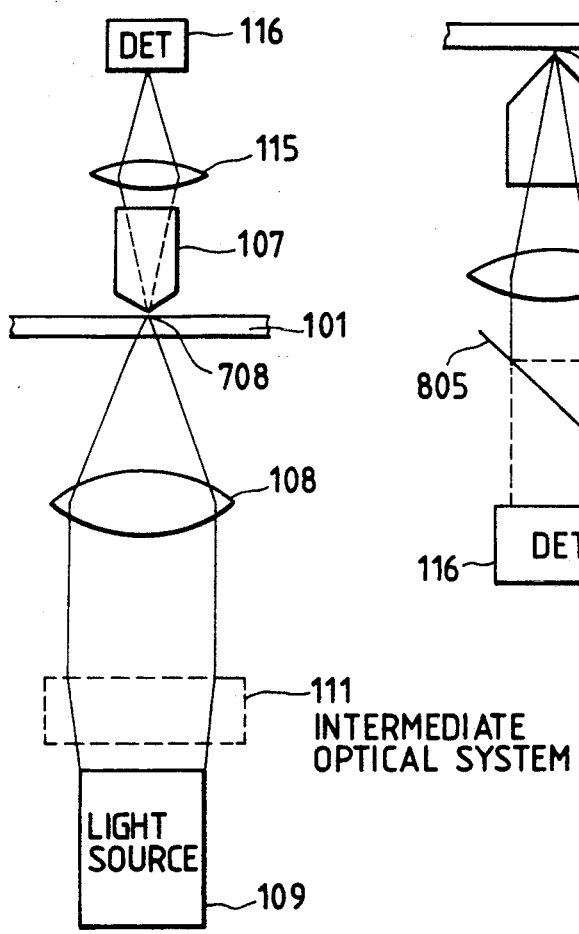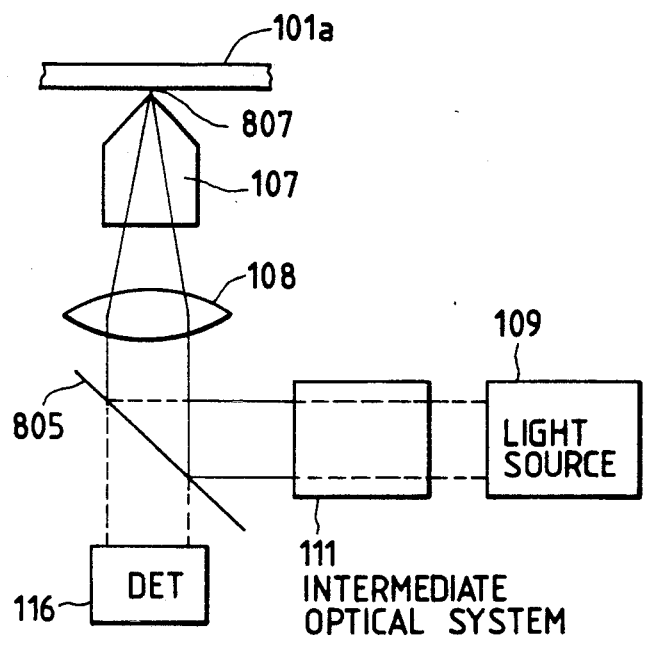

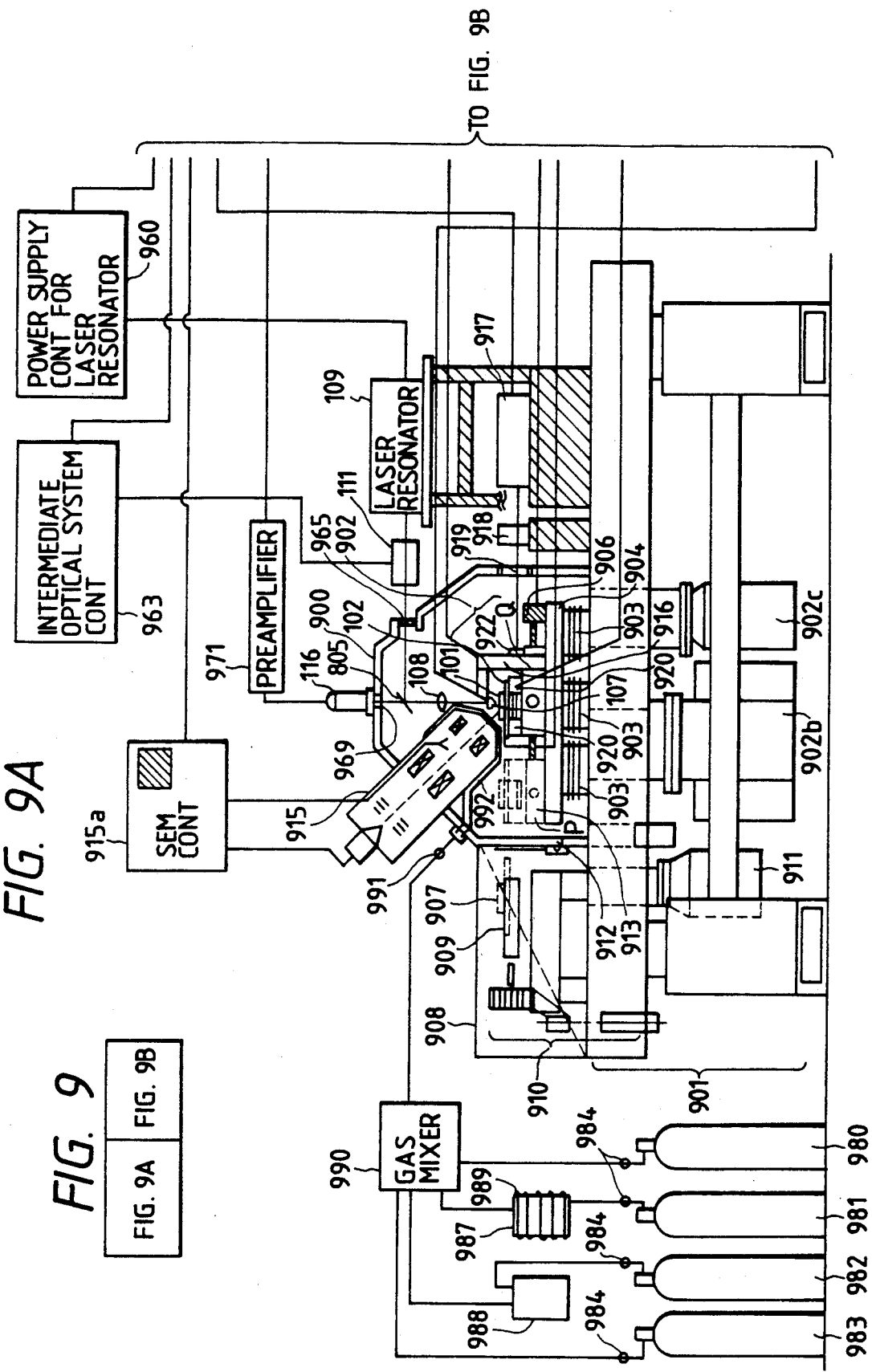

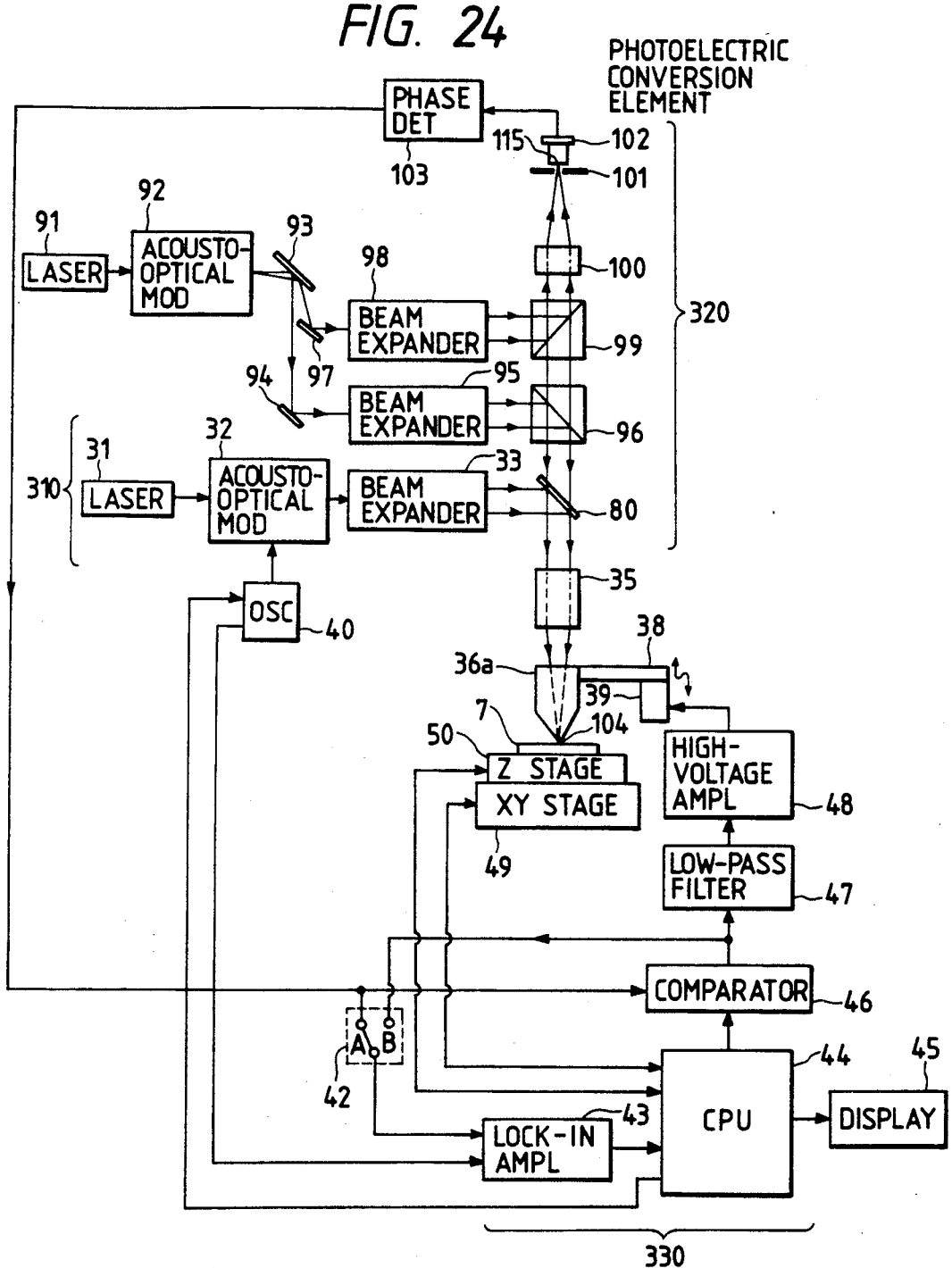

METHOD AND APPARATUS FOR PROCESSING A MINUTE PORTION OF A SPECIMEN

The present invention relates to a minute portion processing method and apparatus and a minute portion analytical method and apparatus for performing various processes such as detecting, analyzing, or processing minute portions, wiring or circuit patterns, or foreign particles of a device or material which are several tens nm in diameter, or film-forming, or annealing.

Furthermore, the present invention relates to a photoacoustic signal detection method and apparatus for detecting the surface of a specimen and internal information using the photoacoustic effect and a method of detecting defects in a semiconductor device element.

As a wiring or circuit pattern of a semiconductor integrated circuit (hereinafter called a LSI) reduces in size to 0.3 $\mu$m, 0.2 $\mu$m, and then 0.1 $\mu$m and is highly integrated, more minute detecting resolution, detection accuracy, correction size, and correction accuracy are required for inspection of defects in the mask pattern, mending or correction of defects, or for detection of defects in a wiring pattern of a LSI and correction of defects. The minimum defect size of a LSI of the 0.3 $\mu$m rule, for example, ranges from 0.1 to 0.05 $\mu$m, and detecting resolution and correction accuracy for defects in such size are required In the case of the 0.1 $\mu$m rule, the minimum defect size is 0.03 $\mu$m, and correction accuracy and detecting resolution for 0.03 $\mu$m or less are required Inspection of minute foreign particles at each stage of the production process of such minute LSI wiring patterns poses problems Foreign particles mixed in the production process cause a reduction in the yield rate. Therefore, it is required to check wafers for foreign particles by sampling inspection and to analyze the composition of the foreign particles. For a process where many foreign particles are mixed, it is required to recheck the production equipment, materials, chemicals, and others to increase the yielding rate.

The minimum size of foreign particles is required to be 0.1 to 0.08 $\mu$m for the 0.3 $\mu$m rule or 0.03 $\mu$m for the 0.1 $\mu$m rule in the same way as above. Since those foreign particles are detected on each wafer pattern, not only high resolution but also a high signal-to-noise ratio are required.

As to analysis of foreign particles, to define the section of the production process and the cause (equipment, materials, chemicals, operators) where and whereby foreign particles are generated and mixed, a high sensitivity and resolution analysis of foreign particles is required. When foreign particles are particularly minute such as less than 0.1 $\mu$m as mentioned above, mean analytical information by a analyzing probe for larger than 0.1 $\mu$m contains background information, foreign particles cannot be analyzed independently, and it is extremely difficult to analyze the composition of foreign particles and define the occurrence cause. Therefore, an analyzing probe for 0.1 to 0.08 $\mu$m is required for LSIs of the 0.3 $\mu$m rule or an analyzing probe for 0.03 $\mu$m or less for LSIs of the 0.1 $\mu$m rule. The above description is only for LSIs. In the information file field such as magnetic disks, optical disks, magneto-optical disks, and bubble memories or in the fields of thin film transistors (TFT) and image sensors, minuteness and high integration are advanced increasingly, and high accuracy and resolution are required for inspection and correction of defects in patterns and production masks or for detection and analysis of foreign particles in the same way as with LSIs.

The minimum rule of LSIs described above is 0.1 $\mu$m. When the LSI size decreases below 0.1 $\mu$m, the so-called quantum effect (the effect based on the quantum theory) starts to appear gradually and the property as an electron wave appears. As a result, the integration increases much the more. In semiconductor device elements with a wiring width narrower than the 0.1 $\mu$m rule, a quantum effect device or an electron wave interference device, wherein the quantum effect is not negated but positively used, is under research and development. This matter is described in detail, for example, in H. Sasaki, "Scattering Suppression and High Mobility Effect of Size-Quantized Electrons in Ultrafine Semiconductor Wire Structures", Japanese Journal of Applied Physics Vol. 19, No. 12, pp. L735–L738.

Devices using this quantum effect are, for example, a quantum ultrafine wire laser and an electron wave interference device. Many devices other than the above two devices have developed. It is important that these devices are operated on condition that they use the electronic quantum effect and the size of major parts such as wires under which the quantum effect can be effectively used should range from 20 nm to several nm.

Therefore, it is definite that the wire width will be smaller than that of LSIs, which are developed at present, by one digit, and a technique for forming such wires stably and highly accurately is a necessary problem for next generation LSIs. Techniques for forming such minute patterns are electron beam lithography and X-ray lithography.

Assuming that an electronic integrated circuit or optical integrated circuit of a such size is formed, detection or correction of defects in the pattern or mask or detection or analysis of foreign particles generated during processing are necessary. For wires 20 nm in width (or the device structure), for example, the defect size is 6 nm and hence the detecting resolution, minimum correction size, correction accuracy, and analyzing probe size should be 6 nm or less. Furthermore, for a device structure of 5 nm, the above four values should be 2 nm or less.

The pattern inspection, pattern correction, and inspection and analysis of foreign particles during processing, which are necessary for production of highly integrated devices, are described above.

There are local detection, analysis, and correction techniques for several $\mu$m or less and detection, correction, and analysis techniques by a laser beam conventionally available.

The method using an electron beam can focus the beam diameter to from 10 nm to several Å. However, the method requires an acceleration voltage of 1 kV or more or 5 kV or more to obtain a particularly fine probe, and poses various problems such as damage to devices, adhesion of foreign particles or contaminants to devices due to the atmosphere in the chamber, the electron beam with a large spot diameter being spread in a specimen in an area of several $\mu$m in diameter, and a reduction in the horizontal and vertical spatial resolution.

As to detection, correction, and analysis by an ultrafine focused ion beam (FIB), as indicated in Yamaguchi et al., U.S. Pat. No. 4,983,540, "Method of Manufacturing Devices Having Superlattice Structures", and the corresponding European Patent Application Publication No. 0 317 952, "Device Having Superlattice Structure, and Method of and Apparatus for Manufacturing the Same", an ion beam from a liquid-metal ion source such as gallium can be focused to a spot 30 to 60 nm in diameter using a reduction lens system comprising two static lenses.

However, this method requires acceleration energy of 1 keV or more and an acceleration voltage of 20 to 50 kV, and is suited to processing by the sputtering phenomenon because ions collide with a specimen, though it causes damage to the peripheral equipment; that is, a problem that the ion beam processes the specimen surface when the position is detected is imposed.

As to this matter, an attempt has been made to minimize the damage processing to a specimen by fetching and reading an image of scanning ion microscopy obtained by one scanning of a focused ion beam (FIB) into an image storage unit, resulting in only a reduction in the above tendency. The focusing limit is possibly about 30 nm due to the magnitude of chromatic aberration by the energy spread of the liquid-metal ion source and the magnitude of effective diameter of the ion source. It is difficult to obtain resolution for a size smaller than 30 nm.

Detection techniques using light (a laser beam is included), which have been developed, are essential to detect device patterns or foreign particles. This is because the reflected light intensity, spectrum, absorption rate, and absorption spectrum of patterns or foreign particles are useful for detection as important information. It is difficult, however, to focus light to each time interval of the wave length. In the wave length zone (infrared 1 $\mu$m to infrared 0.3 $\mu$m) which is useful for the above detection, the spatial resolution limit ranges from 0.1 to 0.2 $\mu$m and it is difficult to detect devices 0.1 $\mu$m or less in diameter.

As an analyzing means, light (a laser beam is included) is a useful means for composition analysis by measuring absorption spectrums of molecular vibration, chemical bond, functional groups, intramolecular or intraatomic electrons, or quasiparticles such as phonon excided plasmor. However, since the spatial resolution is only each time interval of the wave length in the same way as above, it is difficult to correctly analyze foreign particles less than 0.1 $\mu$m in diameter.

Analytical methods for minute portions, which are known at present, are micro-Auger analysis, scanning ion microspectroscopy (SIMS), energy dispersion X-ray spectroscopy (EDX), and an analytical transmission electron microscope (AEM). The micro-Auger analysis focuses an electron beam extremely finely to irradiate it to a specimen. Since the analysis, however, requires a large current at a low acceleration for analysis, it is not suited to the present object requiring analysis of foreign particles less than 0.03 $\mu$m in diameter.

In the SIMS, a probe of 0.05 $\mu$m to 1 $\mu$m can be obtained. A probe of 0.5 $\mu$m to 0.05 $\mu$m is obtained when a high-intensity ion source such as a liquid-metal ion source is used. However, the SIMS poses various problems such that this is a destructive analysis because a specimen is sputtered by ions and the elements of the specimen are analyzed by mass analysis of secondary ions discharged, the method is suited to element analysis but not to compound status analysis, and the equipment is large and expensive because a high performance mass analysis function is required.

In the EDX, the elements of a specimen are analyzed by analyzing X-ray energy discharged from the specimen by irradiating an electron beam. The spatial resolution ranges from 0.5 to 5 $\mu$m because electrons are scattered and spread in the specimen. Therefore, the method is not suited to the object of the present invention.

In the AEM, a transmission electron microscope is used for analysis, the resolution is high such as several Å, and not only the elements but also the chemical bonding status can be checked. However, the AEM poses problems such that thin specimens are required and it takes much time to prepare such specimens. Some materials may not be always cut into thin pieces.

The photoacoustic effect was discovered by Tyndall, Bell, and Röntogen in 1881. This is a phenomenon that when intensity-modulated light (intermittent light) 19 is focused and irradiated to a specimen 7 via a lens 5 as shown in FIG. 25, heat is generated in a photoabsorption area Vop 21 and a thermal diffusion area Vth 23 with a thermal diffusion length $\mu$s 22 is periodically diffused, and surface acoustic waves (ultrasonic waves) are generated by the thermal distortion waves. By detecting the ultrasonic waves or a photoacoustic signal using a microphone (an acoustoelectric transducer), a piezoelectric-crystal element, or a photo-interferometer and obtaining a signal component which is synchronized with the modulation frequency of the incident light, information of the surface and interior of the specimen can be obtained. The detection method for the above photoacoustic signal is discussed, for example, in "Non-Destructive Inspection", Vol. 36, No. 10, pp. 730 to 736 (October, 1987) or IEEE; 1986 Ultrasonic Symposium, pp. 515 to 526 (1986).

Next, the method will be described hereunder with reference to FIG. 26. Parallel light irradiated from a laser 1 is intensity-modulated by an acousto-optical modulation element (acousto-optical modulator) 2, intermittent light thereof is enlarged to a predetermined beam diameter by a beam expander 3, and the enlarged light is reflected off of a half mirror 4 and focused to the surface of a specimen 7 on an XY stage 6 by a lens 5. Ultrasonic waves are generated by thermal distortion waves generated at a focal portion 21 on the specimen 7, and minute displacement occurs on the specimen surface simultaneously. This minute displacement is detected by a Michelson interferometer, which will be described hereunder. Parallel light irradiated from a laser 8 is enlarged to a predetermined beam diameter by a beam expander 9 and separated into two optical paths by a half mirror 10. One of the paths is focused to the focal portion 21 on the specimen 7 by the lens 5. The other is irradiated to a reference mirror 11. The reflected light from the specimen 7 and the reflected light from the reference mirror 11 interfere with each other on the half mirror 10, and the interference pattern is focused to a photoelectric conversion element 13 such as a photodiode by a lens 12. The interference intensity signal which is photoelectrically converted is amplified by a preamplifier 14 and sent to a lock-in amplifier 16. In the lock-in amplifier 16, only the modulation frequency component contained in the interference intensity signal is extracted using a modulation signal from an oscillator 15, which is used for driving the acousto-optical modulation element 2, as a reference signal. This frequency component has information of the surface or interior of the specimen corresponding to the frequency. By changing the modulation frequency, the thermal diffusion length $\mu$s 21 can be changed and information in the specimen depth direction can be obtained. When a defect such as a crack occurs in the thermal diffusion area Vth 23, a signal change appears in the modulation frequency component of the interference intensity signal so as to indicate the presence of such a defect. An XY stage movement signal and an output signal from the lock-in amplifier 16 are processed by a CPU (central processing unit) 17, and a photoacoustic signal at each point on the specimen is outputted to a display 18 such as a monitor TV.

The above prior art is an extremely effective means for detecting photoacoustic signals in the non-contact and non-destructive state, though it has the following problems. The resolution of a photoacoustic signal in the transverse direction is determined by the photoabsorption area Vop 21 shown in FIG. 25, that is, by the spot diameter d (radius) of the laser beam on the specimen 7 given by Equation (1) and the thermal diffusion length $\mu s$ 22 given by Equation (2).

$$d = \frac{1.22\lambda f}{D} \quad (1)$$

where:
$\lambda$: Wave length of the laser beam
f: Focal length of lens 5
D: Diameter of the beam irradiated to lens 5

$$\mu s = \sqrt{\frac{k}{\pi f p c}} \quad (2)$$

where
k: Thermal conductivity of the specimen
$\rho$: Density
c: Specific heat
$f_L$: Intensity modulation frequency of the laser beam When the spot diameter d of the laser beam is smaller than the thermal diffusion length $\mu s$, the resolution in the transverse direction is determined by the thermal diffusion length $\mu s$. When the spot diameter d is larger than the thermal diffusion length $\mu s$, the resolution in the transverse direction is determined by the spot diameter d.

Assuming that, for example, $\lambda = 0.515$ $\mu m$, f=4 mm, and D=6 mm, the spot diameter d of the laser beam obtained from Equation (1) is about 0.42 $\mu m$. When the intensity modulation frequency $f_L$ of the laser beam is 10 kHz, the thermal diffusion length $\mu s$ of, for example, $SiO_2$, which is one of the semiconductor materials, is about 10 $\mu m$ which is obtained from Equation (2). In this case, the thermal diffusion length $\mu s$ is larger than the spot diameter d of the laser beam. Therefore, the resolution $\mu s$ of a photoacoustic signal in the transverse direction is about 10 $\mu m$.

When the intensity modulation frequency $f_L$ of the laser beam is 20 MHz, the thermal diffusion length $\mu s$ of $SiO_2$ is about 0.25 $\mu m$ which is obtained from Equation (2). In this case, the spot diameter d of the laser beam is larger than the thermal diffusion length $\mu s$. Therefore, the resolution d of a photoacoustic signal in the transverse direction is 0.42 $\mu m$.

This means that when the intensity modulation frequency of a laser beam is sufficiently high, the resolution of a photoacoustic signal in the transverse direction is determined by the spot diameter of the laser beam which is exciting light. In the focusing means using the current lens system, the spot diameter d of a laser beam is given by Equation (1), and the limit of d is about 0.3 $\mu m$. In the above prior art, therefore, it is extremely difficult to detect interior information of a specimen having a minute structure of 10 to 100 nm.

When an electron beam is used as an exciting means, it is possible to form a spot 10 nm or less in diameter on a specimen. However, a vacuum chamber is required and it is difficult to simply detect interior information of a specimen in the air. Furthermore, damage to a specimen is another problem. To obtain a minute spot of about 10 nm as mentioned above, an acceleration voltage of about 5 kV is required. In this case, a specimen is damaged and foreign particles or contaminants are adhered to the specimen due to the atmosphere in the chamber, and it is extremely difficult to detect interior information in the non-contact and non-destructive state.

When a focused ion beam (FIB) is used as an exciting means, it is possible to form a spot of 30 to 60 nm, though a vacuum chamber is required in the same way as an electron beam. An acceleration voltage of 20 to 50 kV is also required, and it is impossible to prevent specimens from damage in the same way as an electron beam.

One of the objects of the present invention is to provide a method and apparatus for processing a minute portion and a method and apparatus for analyzing a minute portion for detecting and correcting pattern defects on the surface or in the interior of an element or substrate with a spatial resolution of 20 nm or less and for detecting and analyzing foreign particles so as to solve the above problems.

Another object of the present invention is to provide a minute portion processing method and apparatus and a minute portion analytical method and apparatus for performing various processes such as detecting, analyzing, or processing minute portions, wiring or circuit patterns, or foreign particles of a device or material which are several tens nm in diameter, or film-forming, or annealing.

A further object of the present invention is to provide a photoacoustic signal detection method and apparatus for detecting internal information of a specimen sensitively with a high detection resolution of 10 to 100 nm for photoacoustic signals in the non-contact and non-destructive state.

According to the present invention, defects in element patterns ranging from several tens nm in diameter to the atomic size are detected, corrected, or analyzed by using a near-field optical scanning microscope separately or a scanning tunneling microscope combined as a means for detecting, correcting, or analyzing defects in element patterns.

The near-field optical scanning microscope (hereinafter may be abbreviated to NOSM) is on the basis of the principle that when an aperture with a diameter of one-several-tenth to one-several-hundredth of the light wave length is placed at a distance equal to the aperture size from an object, light exists only in an area with a diameter equal to the aperture size in the so-called evanescent wave area (a near field) which is emitted from the aperture when intensive light such as a laser beam is irradiated. This matter is described in U. Dürig et al., "Near Field Optical Scanning Microscope", Journal of Applied Physics, Vol. 59, No. 10, pp. 3318 to 3327 (1986).

In this case, light exists only in an area equal in diameter to the aperture size. Therefore, when the aperture is made smaller and the distance between the object and the aperture is made close to the aperture size, the resolution is improved. However, it is practically impossible to make the resolution smaller than the penetration depth of light wave into the interior of the aperture material. An aperture material with a shallow penetration depth is a metal. The penetration depth (so-called skin depth) in this case is about 10 nm.

When a laser beam is irradiated to an object as a spot of about 10 nm by this method and the reflected light, transmitted light, and scattered light from the object are removed, a spatial resolution of about 10 nm can be obtained. When the object and the aperture are moved relatively by using a piezoelectric actuator in the same way as with the scanning tunneling microscope so as to allow the light to scan the area where the object exists and the distance between the aperture and the object is kept almost constant during scanning, the light probe can scan a wide area on the object. By synchronizing a signal, which is obtained by detecting the reflected light, transmitted light, or scattered light from the object during scanning, with the scanning and displaying it on the display, an object image or signal image is obtained and the object can be detected or observed.

In the present invention, element patterns are detected, pattern defects are detected, or foreign particles on elements are detected using the NOSM. Infrared rays, visible rays, or ultraviolet rays are used as a laser beam, or particularly a dye laser with a wide wave length zone is used. By changing the wave length using an etalon, an absorption spectrum or a reflection spectrum of a portion of about 10 nm of an element or a foreign particle of about 10 nm on an element is obtained and the composition can be analyzed.

According to the present invention, only an extremely narrow area of about 10 nm of an element is heated by a laser beam inputted into the NOSM and various processes such as local annealing of an ion implanted area, local recrystallization of a polycrystalline, and removal processing by local bumping or evaporation can be performed.

According to the present invention, the aperture and object are filled with gas or liquid, a laser beam is irradiated to the object in this state so as to decompose the gas or liquid, and the component is deposited locally on the object so as to locally form a film. A nozzle is installed near a specimen and the opening of a light transmission body of the NOSM, and gas can be sprayed during light irradiation. The above gas is a gas for chemical vapor deposition (CVD) of a metal such as an organometal compound, for example, alkyl metal, metal carbonyl, or metal alkoxide or metal halide. The above gas is a gas for chemical vapor deposition of silicon dioxide such as tetraethoxy silane or diethyl silane, or a gas combined with an oxidizing agent gas such as oxygen or hydrogen peroxide.

According to the present invention, the NOSM is combined with the scanning tunneling microscope (hereinafter, may be abbreviated to STM) and the combined equipment is used as specified in 111 to 122 indicated below. The present invention provides a minute portion processing method and apparatus for detecting a minute portion of an element or a substrate by the near-field optical scanning microscope and for processing, film-forming, or annealing the detected minute portion with the scanning tunneling microscope. The present invention provides a minute portion processing method and apparatus for detecting a minute portion of an element or a substrate by the scanning tunneling microscope and for processing, film-forming, or annealing the detected minute portion with the near-field optical scanning microscope. The present invention provides a minute portion processing method and apparatus for detecting a minute portion of an element or a substrate by the near-field optical scanning microscope and for performing sputtering processing for the detected minute portion with a focused ion beam-processing system, CVD film-forming, or ion beam implantation. The present invention provides a minute portion analyzing method and apparatus for detecting a minute portion of an element or a substrate by the near-field optical scanning microscope and for analyzing the detected minute portion with the scanning tunneling microscope or scanning tunneling analyzer. The present invention provides a minute portion analyzing method and apparatus for detecting a minute portion of an element or a substrate by the scanning tunneling microscope and for analyzing the detected minute portion with the near-field optical scanning microscope.

The STM and STS (scanning tunneling spectrometer) are described in detail, for example, in Y. Kuk and P. J. Silverman, "Scanning Tunneling Microscope Instrumentation", Review of Scientific Instruments, Vol. 60, No. 2, pp. 165 to 180 (1989) or K. Kajimura, et al., "Scanning Tunneling Microscope", Solid Physics, Vol. 22, No. 3, pp. 176 to 186 (1987). Means for partially processing elements and forming films using the STM are described in Yamaguchi et al., U.S. patent application Ser. No. 07/455,155, filed on Dec. 22, 1989, "Method and Apparatus for Processing a Fine Pattern", and the corresponding European Patent Application Publication No. 0 376 045.

111: The position of an element is detected by the NOSM, and a special part is subjected to processing, film-forming, or annealing by the STM on the basis of the information.

112: The position of an element is detected by the NOSM, and a special part is analyzed by the STM or STS on the basis of the information.

121: The position of an element is detected by the STM, and a special part is subjected to processing, film-forming, or annealing by the NOSM on the basis of the information.

122: The position of a special part is detected by the STM and analyzed by the NOSM.

By the above configuration, a minute portion ranging from 20 nm to the atomic size can be detected, processed, film-formed, annealed, or ion-implanted, atoms or molecules can be removed or inserted, or foreign particles or defects can be analyzed.

ROMs (read only memory) or RAMs (random access memory) can be directly manufactured. Data can be written into or deleted from a memory device. Defects including foreign particles of 20 nm or less existing on the surface of a wafer or element or in the interior thereof can be detected or analyzed.

Furthermore, the present invention realizes high resolution and highly sensitive detection of a photoacoustic signal by using a near-field optical scanning microscope as a means for exciting a specimen so as to generate the photoacoustic effect and by using a photointerferometer comprising a scanning tunneling microscope or a near-field optical tunneling microscope so as to detect a minute displacement of the specimen surface generated by the photoacoustic effect.

The near-field optical scanning microscope (NOSM) is on the basis of the principle that when an aperture with a diameter of one-several-tenth to one-several-hundredth of the light wave length is placed at a distance equal to the aperture size from the specimen, light exists only in an area with a diameter equal to the aperture size in the so-called near field where an evanescent wave is emitted from the aperture when intensive light such as a laser beam is irradiated. This matter is described in the foregoing journal.

In this case, light exists only in an area equal in diameter to the aperture size. Therefore, when the aperture is made smaller and the distance between the specimen and the aperture is made close to the aperture size, the resolution is improved. However, it is practically impossible to make the resolution smaller than the penetration depth of light wave into the interior of the aperture material. An aperture material with a shallow penetration depth is a metal. The penetration depth (so-called skin depth) in this case is about 10 nm.

Therefore, a laser beam can be irradiated to a specimen as a spot of about 10 nm by this near-field optical scanning microscope. Furthermore, when the aperture and specimen are relatively scanned two-dimensionally with the distance between the two kept constant, the specimen can be excited two-dimensionally at a resolution of about 10 nm and the photoacoustic effect can be generated in the high resolution state.

Furthermore, when the gap between the aperture of the near-field optional scanning microscope and a specimen is changed, light is reflected off of the specimen surface and the light quantity passing through the aperture is changed. Therefore, by observing the intensity of the reflected light passing through the aperture, the minute displacement generated on the specimen surface by the photoacoustic effect can be detected as a change in the gap. The scanning tunneling microscope (STM) is described in detail in the foregoing literature.

To accomplish the above object, in a photoacoustic signal detection apparatus of the present invention, comprising a light source, a modulation means for modulating the intensity of light from said light source at a predetermined frequency, an exciting means for exciting the specimen by focusing the modulated light on the specimen, a detection apparatus for detecting the photoacoustic effect generated by the specimen, and an information extraction means for extracting information of the specimen surface and interior from the detection signal detected by said detection apparatus, the above exciting means comprises a near-field optical scanning microscope so as to improve the resolution of a photoacoustic signal in the transverse direction.

Furthermore, to accomplish the above object, in the above photoacoustic signal detection apparatus of the present invention, the above exciting means comprises a near-field optical scanning microscope and the above detection apparatus for detecting the photoacoustic effect comprises a scanning tunneling microscope for detecting a minute displacement generated on the specimen surface by the photoacoustic effect so as to improve the resolution of a photoacoustic signal in the transverse direction and the detection sensitivity.

Furthermore, to accomplish the above object, in the above photoacoustic signal detection apparatus of the present invention, the above exciting means comprises a near-field optical scanning microscope and the above detection apparatus for detecting the photoacoustic effect comprises a near-field optical scanning microscope for detecting a minute displacement generated on the specimen surface by the photoacoustic effect so as to improve the resolution of a photoacoustic signal in the transverse direction and the detection sensitivity.

Furthermore, to accomplish the above object, in the above photoacoustic signal detection apparatus of the present invention, the above exciting means comprises a near-field optical scanning microscope and the above detection apparatus for detecting the photoacoustic effect comprises a photo-interferometer using a scanning tunneling microscope for detecting a minute displacement generated on the specimen surface by the photoacoustic effect so as to improve the resolution of a photoacoustic signal in the transverse direction and the detection sensitivity.

Since the exciting means of the photoacoustic signal detection apparatus comprises a near-field optical scanning microscope, a minute optical spot of 10 to 100 nm can be formed on a specimen and the photoacoustic effect can be generated in a local area of 10 to 100 nm. By doing this, the resolution of a photoacoustic signal in the transverse direction can be extremely improved.

Furthermore, since the exciting means comprises a near-field optical scanning microscope and the detection apparatus for detecting the photoacoustic effect comprises a scanning tunneling microscope, the resolution of a photoacoustic signal in the transverse direction and the detection sensitivity can be extremely improved.

Furthermore, since the exciting means comprises a near-field optical scanning microscope and the detection apparatus for detecting the photoacoustic effect also comprises a near-field optical scanning microscope, the resolution of a photoacoustic signal in the transverse direction and the detection sensitivity can be extremely improved.

Furthermore, since the exciting means comprises a near-field optical scanning microscope and the detection apparatus for detecting the photoacoustic effect comprises a photo-interferometer using a near-field optical scanning microscope, the resolution of a photoacoustic signal in the transverse direction and the detection sensitivity can be extremely improved.

In the accompanying drawings:

FIG. 1 is a basic schematic view of an apparatus for detecting and correcting minute patterns or detecting and analyzing foreign particles using a combination of a NOSM and STM relating to the present invention;

FIGS. 2(a) to 2(f) are drawings showing an embodiment for preparing a NOSM tip;

FIGS. 3(a) and 3(b) are drawings showing another embodiment for preparing a NOSM tip;

FIG. 7 is a drawing showing an embodiment that a NOSM tip is mounted on the detection side;

FIG. 8 is a drawing showing an embodiment that reflected light from a specimen is detected using a NOSM tip;

Figure 12A:
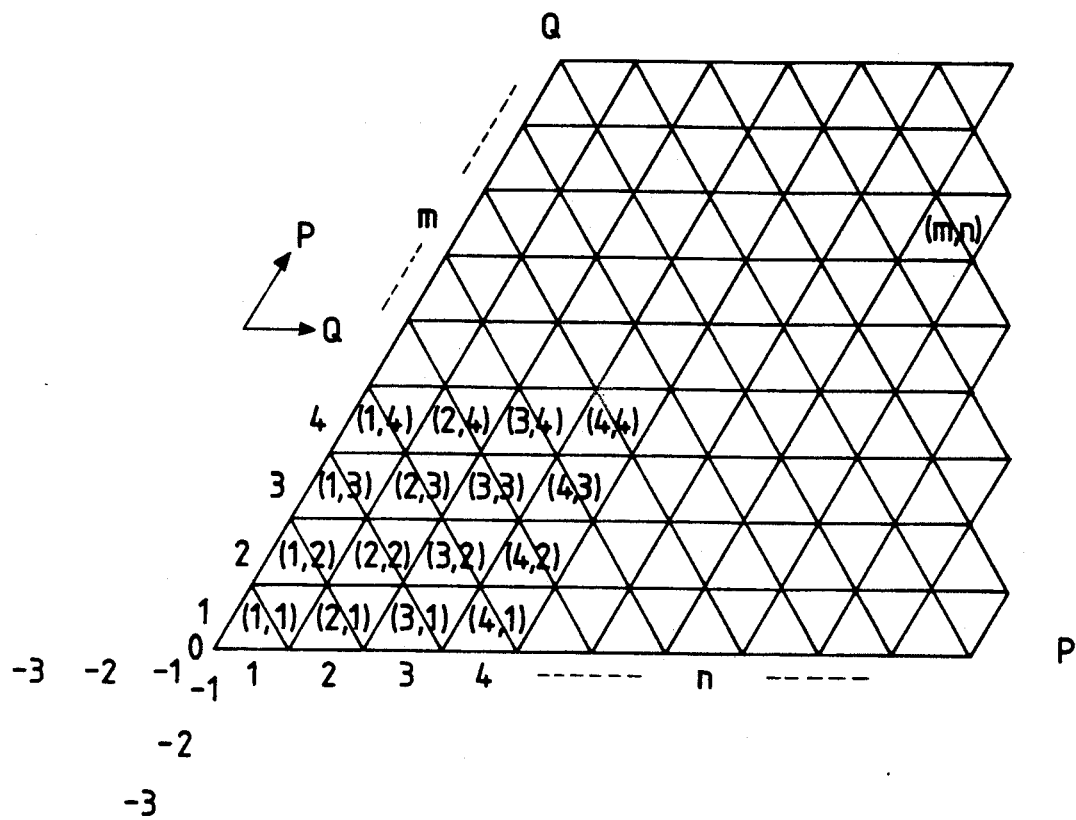
Figure 12B:
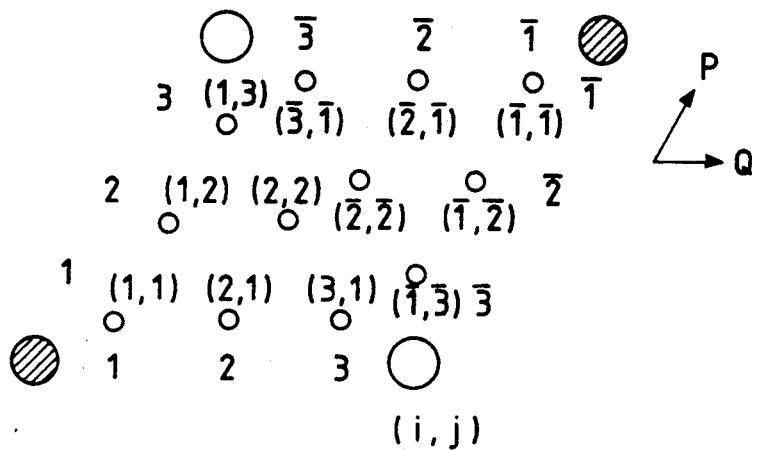
Figure 13:
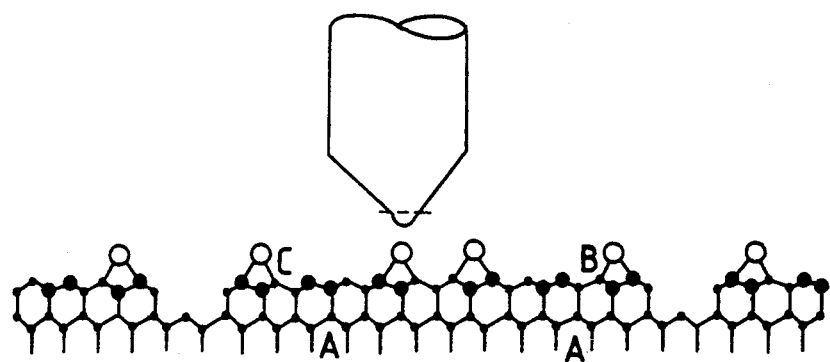
Figure 15A:
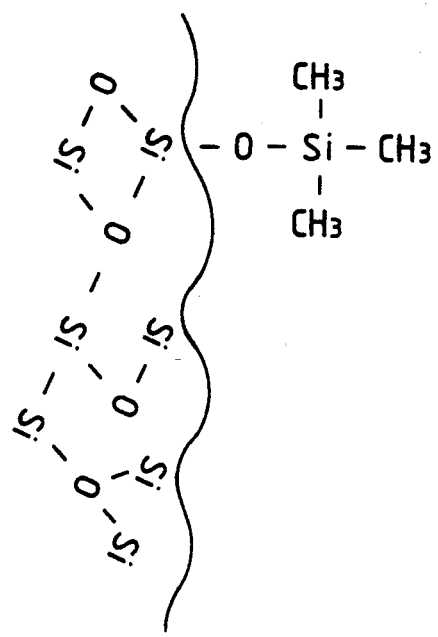
Figure 15B:
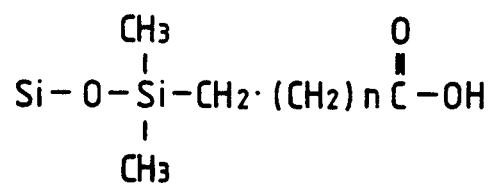
Figure 15C:
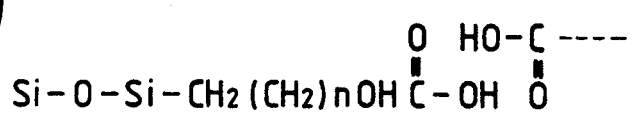
Figure 16A:
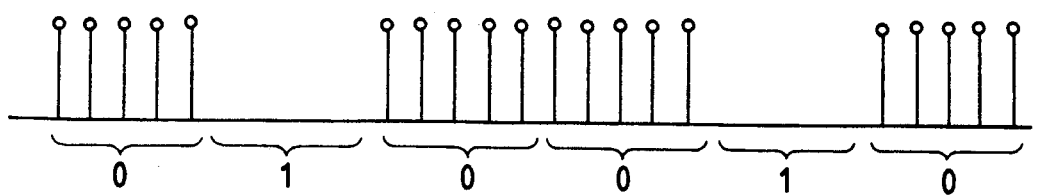
Figure 16B:
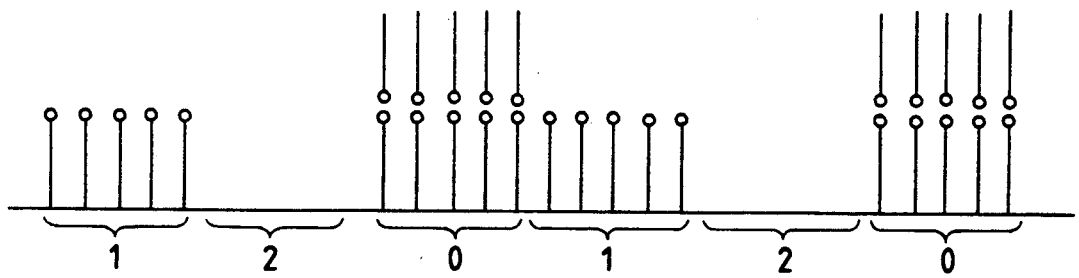
Figure 17:
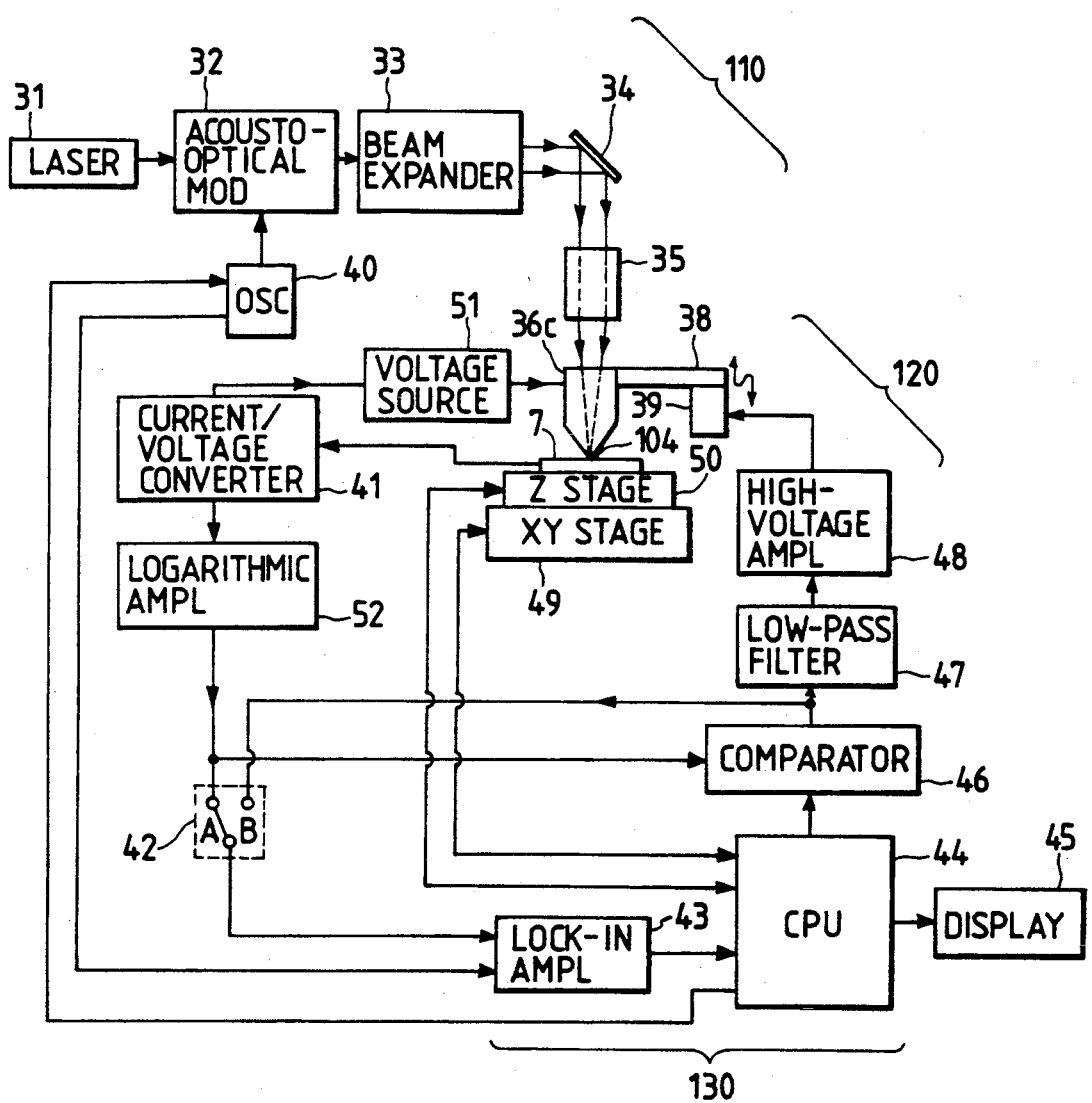
Figure 19:
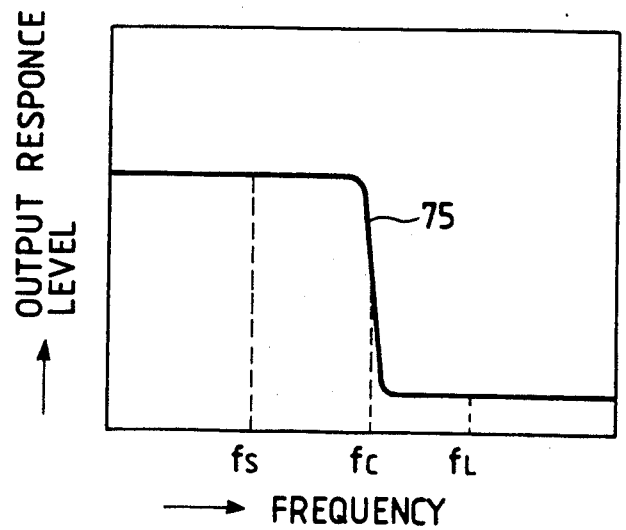
Figure 20:
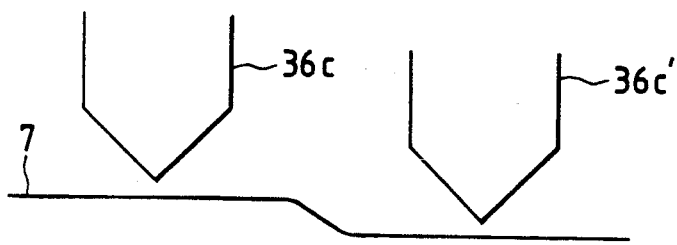
Figure 21:
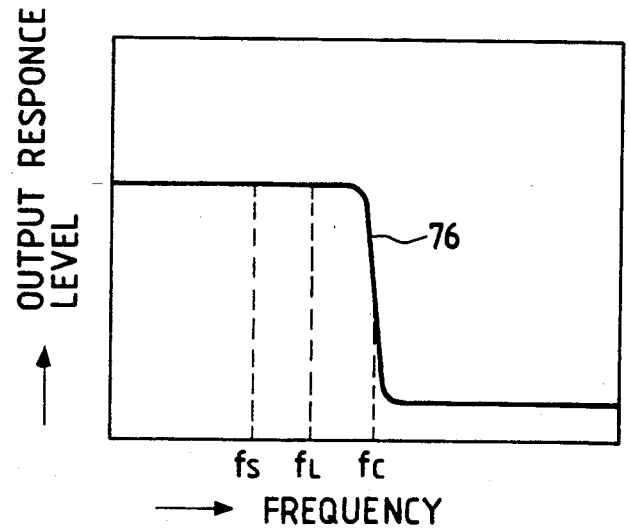
Figure 22:
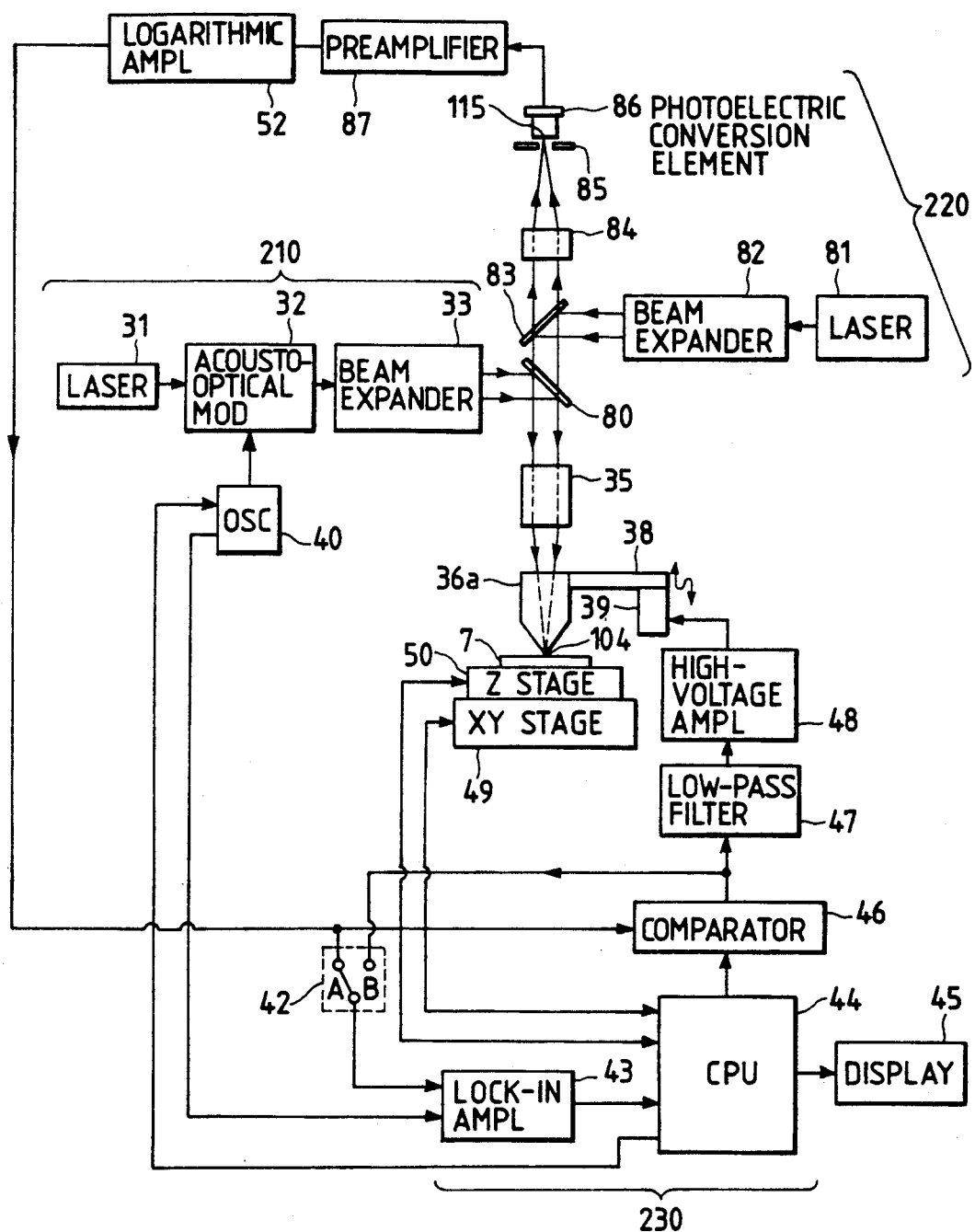
Figure 23:
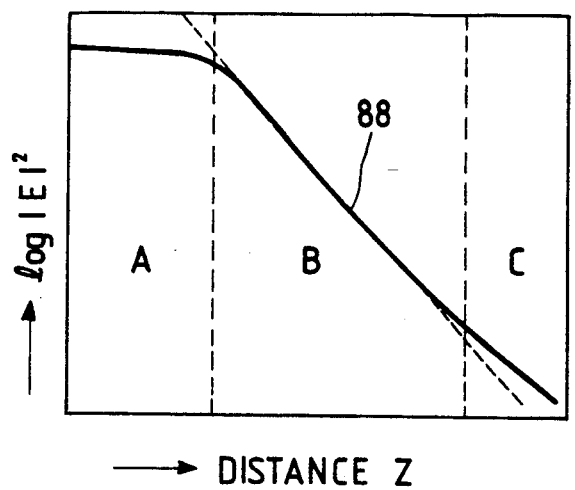
Figure 25:
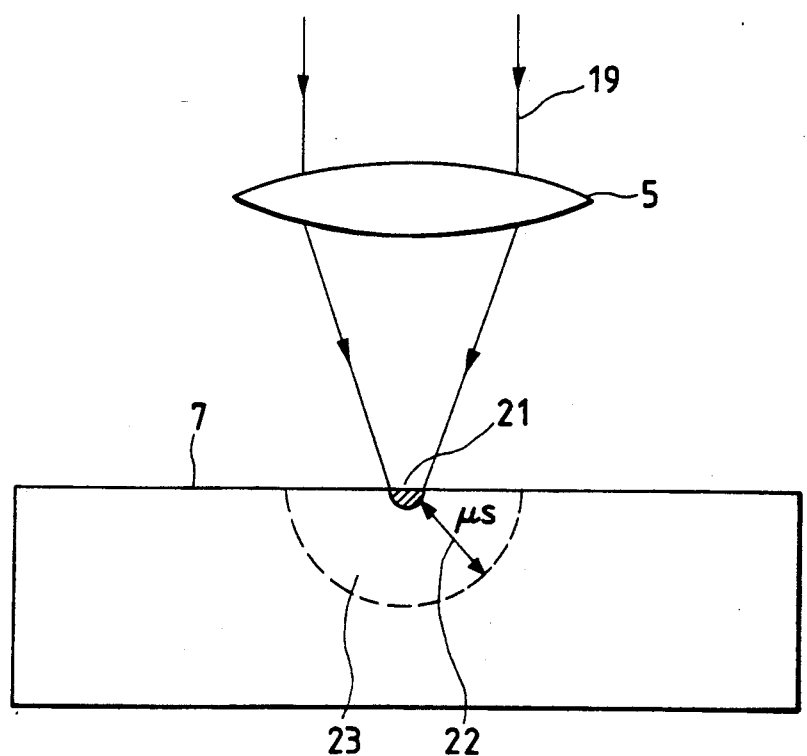

FIGS. 12(a) and 12(b) are drawings showing the atom configuration of the (111) surface of Si which is cut from the front;

FIG. 13 is a drawing showing the section of the atom configuration of the (111) surface of Si and the needle tip of a STM;

FIGS. 14(a) to 14(e) are drawings for explaining an embodiment of the present invention which is applied to a memory device;

FIGS. 15(a) to 15(c) are drawings for explaining an embodiment that a LB film is formed using the present invention;

FIGS. 16(a) and 16(b) are drawings showing an embodiment of the present invention that data is stored in a memory device wherein 5 molecules constitute one bit;

FIG. 17 is a drawing showing the first and second embodiments of a photoacoustic signal detection apparatus of the present invention;

FIGS. 18(a) to 18(f) are drawings showing NOSM tip types;

FIG. 19 is a drawing showing the relationship between the frequency characteristics of a low-pass filter in the first, third, and fifth embodiments of a photoacoustic signal detection apparatus of the present invention, the sampling frequency of a detected signal, and the modulation frequency of a laser beam;

FIG. 20 is a drawing showing the following state of a NOSM tip for an uneven specimen;

FIG. 21 is a drawing showing the relationship between the frequency characteristics of a low-pass filter in the second, fourth, and sixth embodiments of a photoacoustic signal detection apparatus of the present invention, the sampling frequency of a detected signal, and the modulation frequency of a laser beam;

FIG. 22 is a drawing showing the third and fourth embodiments of a photoacoustic signal detection apparatus of the present invention;

FIG. 23 is a drawing showing the relationship between the gap distance between a NOSM tip and a specimen and the transmitted light quantity of the aperture of the NOSM tip;

FIG. 24 is a drawing showing the fifth and sixth embodiments of a photoacoustic signal detection apparatus of the present invention;

FIG. 25 is a drawing showing the principle of the photoacoustic effect; and

Figure 26:
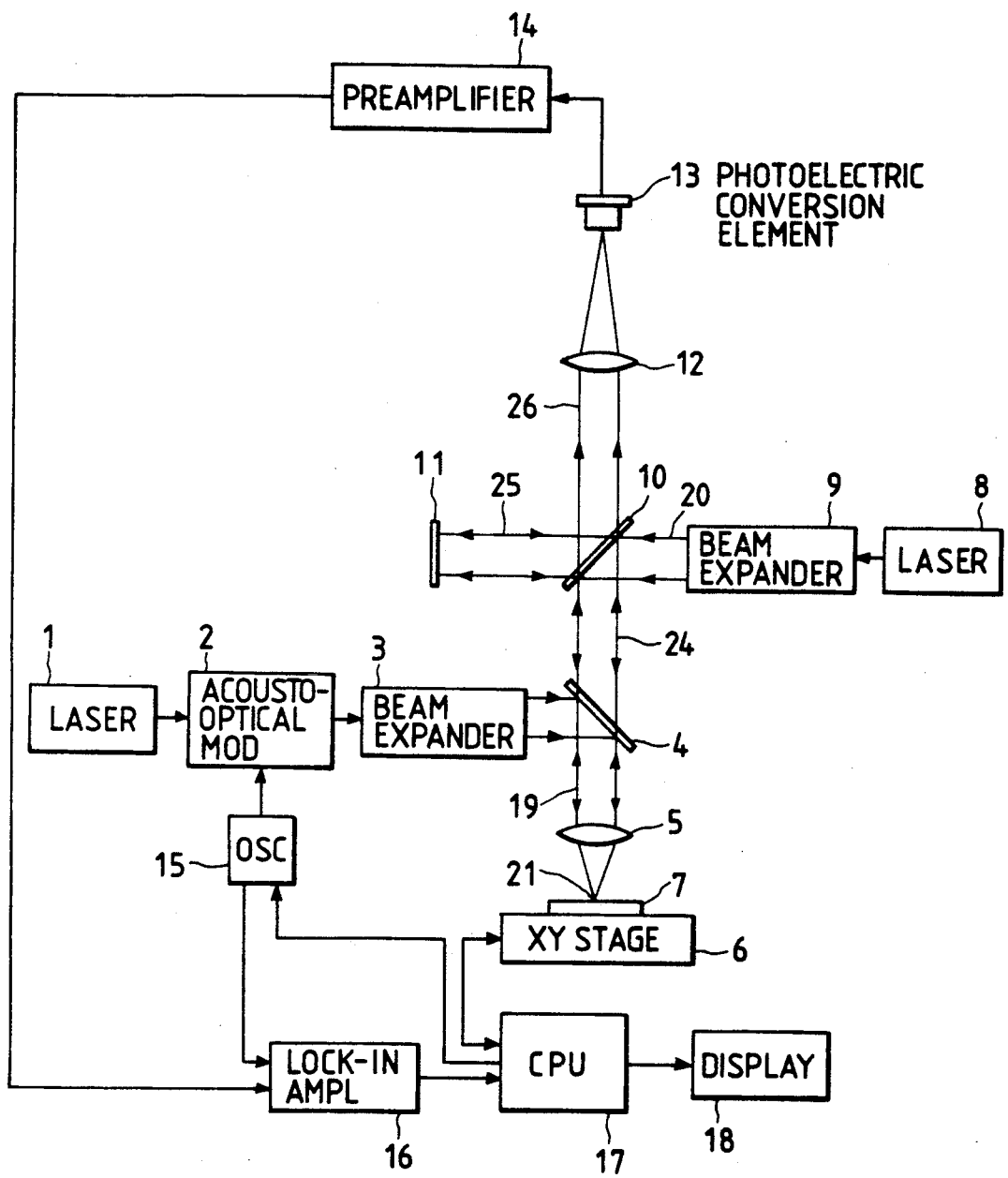

FIG. 26 is a drawing showing a conventional photoacoustic signal detection apparatus.

Figure 1:
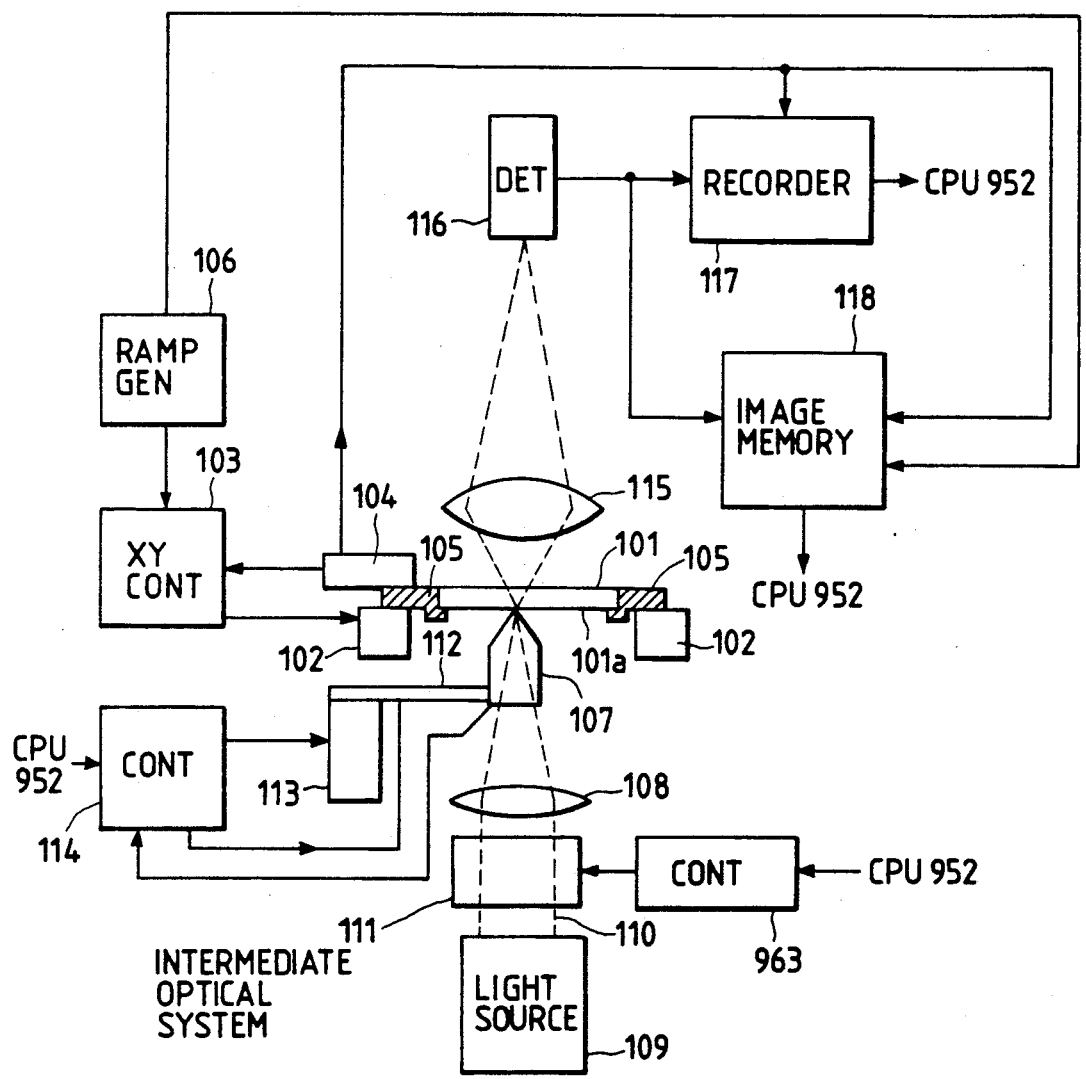

Next, the present invention will be described in detail on the basis of the embodiments shown in the drawings. FIG. 1 is a basic schematic view of an apparatus for detecting and correcting minute patterns or detecting and analyzing foreign particles using a combination of a NOSM and STM relating to the present invention.

In FIG. 1, a specimen, for example, LSI 101 is placed on a specimen table 105 with a pattern portion 101a for detection, correction, or analysis down. An XY scanner 102 is an actuator of the bielectrode type or the bielk type using the piezoelectric effect or the electrostrictive effect, and moves on the specimen table 105 in the X or Y direction with the accuracy of less than 1 nm according to the applied voltage by an XY controller 103 on the basis of the power of a ramp generator 106. So as to eliminate the hysteresis of a piezoelectric element or an electrostrictive element or the creep effect, the absolute position is measured by an XY position sensor 104, a negative feedback is applied to the XY controller 103, and the specimen is moved to a correct position. The XY position sensor 104, for example, comprises a light source such as a light emitting diode mounted to the equipment body, a pin hole mounted to the specimen table 105, and a photodetector mounted to the equipment body, and has position detection accuracy of less than 5 nm. In this case, a laser interferometer of the specimen table 105 or a STM, or both of them may be used to measure the position.

Figure 2A:
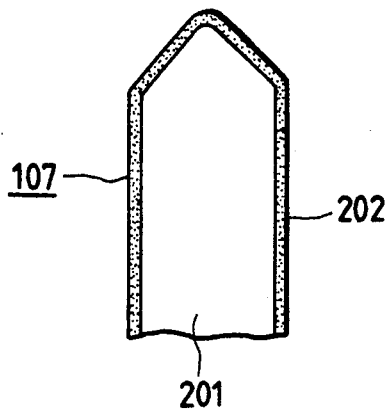
Figure 2B:
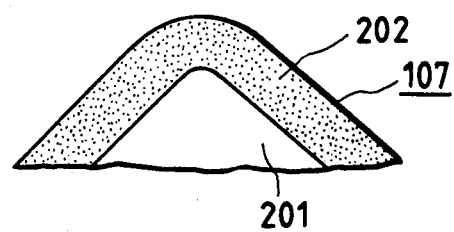
Figure 2C:
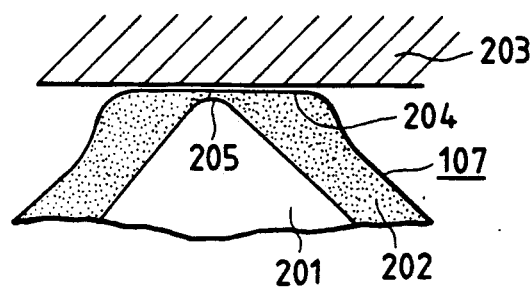

An output 110 of a light source 109 such as a laser passes through an intermediate optical system 111 connected to an intermediate optical system controller 963, focused by a lens 108, and sent to a NOSM tip 107. The NOSM tip 107 is a quartz glass rod 201 with a tip polished sharply to about 10 nm as shown in FIG. 2(a) and FIG. 2(b) (an enlarged view of the tip) which is deposited with a highly conductive metal thin film 202. When the quartz glass rod is pressed against a flat surface 203, deposited metal 204 at the tip is spread flatwise on the flat surface 203, the deposited metal film 204 at the tip 205 of the glass rod 201 becomes thinner than the so-called skin depth or is removed, causing the glass rod to be exposed. When light is irradiated from the bottom in this state, the light can pass through an extremely narrow area (aperture) of the tip. By doing this, a NOSM tip comprising a sharp tip, an aperture formed at the tip, and an opaque coating around the aperture is formed. The NOSM tip is a needle-shaped light transmission body which is formed so that light passes through only an extremely narrow area of about 10 nm of the tip. The type of the NOSM tip 107 may be different from the type shown in FIGS. 2(a) to 2(f). FIGS. 3(a) and tube is melted, lengthened, and cut into pieces. The glasswork technique is required for production. It is possible to produce a tip having a tip portion 302 L which is narrow as shown in FIG. 3(a) and an aperture 303 which is narrow such as 10 nm as shown in the same drawing. By depositing a metal thin film on the surface thereof, a NOSM tip 107 can be formed.

Figure 6:
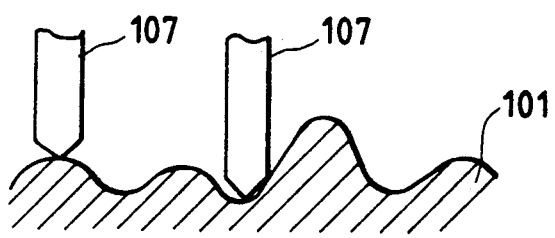
FIG. 6 is a drawing showing an embodiment that a NOSM tip moves up and down according to the uneven surface of a specimen.

Since the tip of a NOSM tip formed in this way is sharp, even if the variation range of an uneven surface of a specimen is wide as shown in FIG. 6, the distance between the aperture 303 at the tip and the specimen surface can be kept always at a size nearly equal to the diameter of the aperture 303 by moving the NOSM tip up and down like numerals 107 and 107. The distance between the tip of the NOSM tip 107 and the specimen surface shown in FIG. 1 is controlled by a piezoelectric element 112 in the Z direction and a drive motor 113 in the Z direction.

The light 110 from the light source is focused by the lens 108, transmits through the aperture at the tip and the specimen 101, focused by a focusing lens 115, and sent to a detector 116. By measuring the intensity of the detected light at a location with no pattern provided, the distance between the aperture at the tip of the NOSM tip 107 and the specimen surface can be measured. By an instruction provided from a CPU (central processing unit) 952 to a controller 114 on the basis of this intensity, the drive motor 113 in the Z direction or the piezoelectric element 112 in the Z direction can be driven so as to keep the distance constant. Particularly, the distance of the tip is important, and a tunnel current can be used to keep the accuracy at 1 nm or less.

Figure 2D:
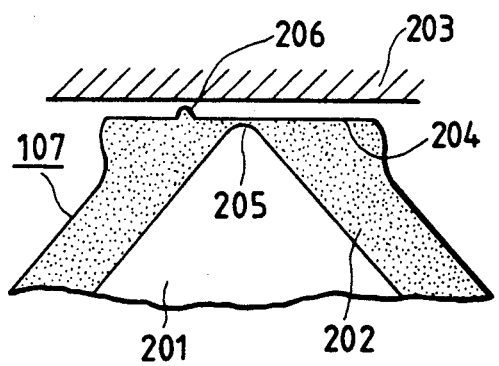
Figure 2E:
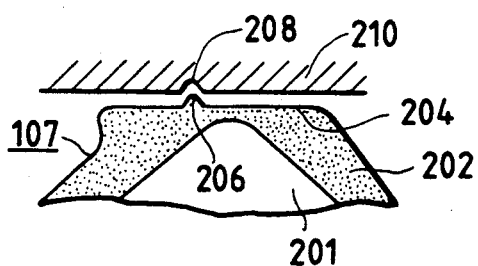
Figure 3A:
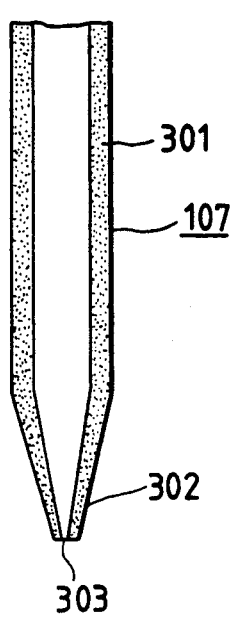
Figure 3B:
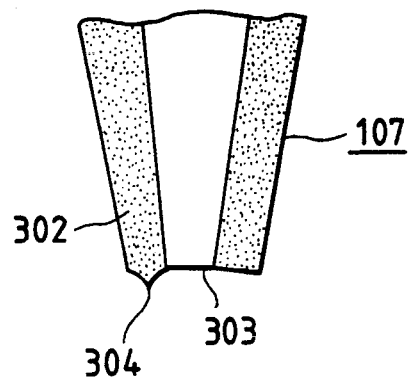

A NOSM tip 107, which is pressed and spread, having a minute protrusion 206 at the metal deposited part at the tip thereof as shown in FIG. 2(d) is produced. This protrusion can be formed by pressing the metal film against a flat die with a minute hollow 208 as shown in FIG. 2(e) when pressing a needle to a flat surface as shown in FIG. 2(c). By applying a high voltage to the metal film, for example, by heating it locally by irradiation of a laser beam or power supply after a flat portion is formed as shown in FIG. 2(c), a minute protrusion 206 can be formed as shown in FIG. 2(e). For a NOSM tip 107 of the pipette type shown in FIG. 3(a), a minute protrusion 304 can be formed at the tip in the same way as shown in FIG. 3(b).

When the atoms at the tip of the minute protrusion 206 or 304 formed in this way are close to the atoms of the specimen surface and the distance becomes about 2 nm, a tunnel current starts flowing by application of several volts. The needle approaches the specimen by applying several volts between the metal film of the NOSM tip 107 and the pattern of the specimen 101 and stops approaching when a tunnel current is detected. A tunnel current flowing when there is a potential difference of V between a tip, which is at a distance of Z from a surface of a work function $\phi$, and the surface is expressed by the following equation (3):

$$It = \frac{AV}{Z} \exp(-BZ\sqrt{\phi}) \quad (3)$$

where symbols A and B are constants.

Therefore, the distance Z can be controlled with extremely high accuracy so as to keep the current It constant.

Figure 2F:
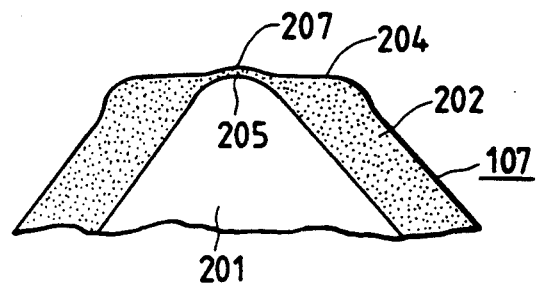

In FIG. 2(f), a minute protrusion 207 is provided at the center of the tip of the NOSM tip 107 in the same way as above. There is an advantage in this case that the distance between the tip and the specimen can be detected immediately by a tunnel current. This provides an advantage that the process by this tunnel current and the optical process by the NOSM can be performed simultaneously or at the same location as described later.

Figure 4:
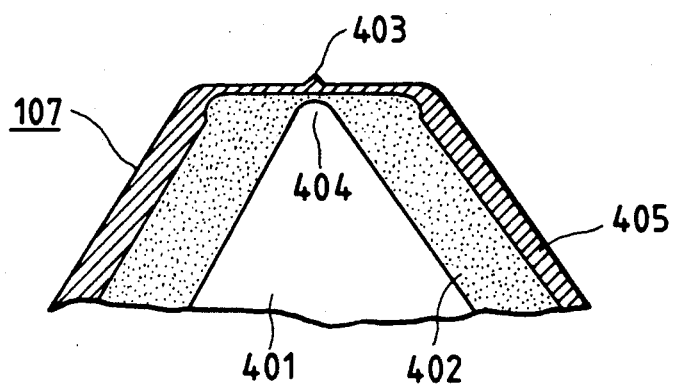
FIG. 4 is a drawing showing a further embodiment for preparing a NOSM tip.

FIG. 4 shows another example that a minute protrusion 403 flowing a tunnel current is provided at the center of the tip of the NOSM tip 107 in the same way as in FIG. 2(e). In this case, a glass tip 401 is coated with a metal thin film 402 and pressed against a flat surface so as to spread the tip. Then, a transparent conductive layer 405, for example, $SnO_2$ or $In_2O_3$ is deposited on the spread tip, and pressed against a flat surface with a hollow like 208 so as to spread. By doing this, a protrusion 403 is provided at the location corresponding to the tip 404 of the glass tip 401. There is an advantage that since the tip 107 uses the transparent conductive layer 405, variations in the wave front at the protrusion can be minimized. Particularly, when the refractive index of the transparent conductive layer 405 is made equal to that of the atmosphere between the NOSM tip 107 and the specimen 101, for example, air, variations in the above wave front can be minimized, and the effect of the minute protrusion 403 on the light behavior can be almost eliminated. The tip 404 is an aperture.

Figure 5:
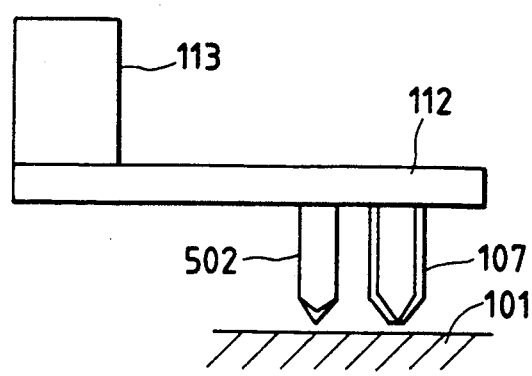
FIG. 5 is a drawing showing an embodiment that a NOSM tip and a STM tip are mounted independently to a piezoelectric element.

FIG. 5 shows another embodiment for accomplishing the same object, and the NOSM tip 107 and the STM tip 502 are mounted to the piezoelectric actuator 112 in the Z direction. By doing this, the distance between the tip and the specimen 101 can be measured and controlled by measuring a tunnel current in the STM tip 502.

As described later, the process by the STM can be performed at the same location of the specimen as the process by the NOSM by moving the specimen table 105 and the tip relatively by the distance between the tips of the NOSM tip 107 and the STM tip 502.

In the method described above with reference to FIG. 1, the light of the NOSM 107 is irradiated to one side of the specimen 101, and the transmitted light is focused by the lens 115 and detected by a detector 116 such as a photomultiplier. Numeral 117 indicates a recorder and 118 an image memory. The tested intensity can be displayed on the recorder 117 or the display of the image memory 118 in synchronization with the output of the ramp generator 106 or of the position sensor 104. The results can be outputted to the CPU 952.

To detect the transmitted light in the above case, a specimen is required to transmit light like a photo-mask. Device elements such as LSI wafers are opaque specimens, and it is required to use the reflected light for the NOSM for them as shown in FIG. 8. In this case, the output of the light source 109 such as a laser passes through the intermediate optical system 111, is reflected off of a half mirror 805, focused by the focusing lens 108, passes through an aperture 807 at the tip of the NOSM tip 107, and is reflected off of the surface of the specimen 101a. The reflected output passes through the aperture 807, the lens 108, and the half mirror 805 and is detected by the detector 116 such as a photomultiplier.

Since the reflected light can be detected in this case, the specimen 101a may be opaque. For an opaque specimen, the reflected light can be detected by this method. The other points are the same as those specified in FIG. 1.

For the transmitted light, a method that the NOSM tip 107 is mounted on the opposite side to the light source 109 for the specimen 101 as shown in FIG. 7 can be used. In this case, the light from the light source 109 such as a laser passes through the intermediate optical system 111 and is focused by the focusing lens 108 so as to form a minute spot 708 on the specimen 101 on the NOSM tip side. The transmitted light passes through the aperture at the tip of the NOSM tip 107, is focused by the lens 115, and detected by the detector 116. The other points are the same as those specified in FIG. 1.

Figure 9B:
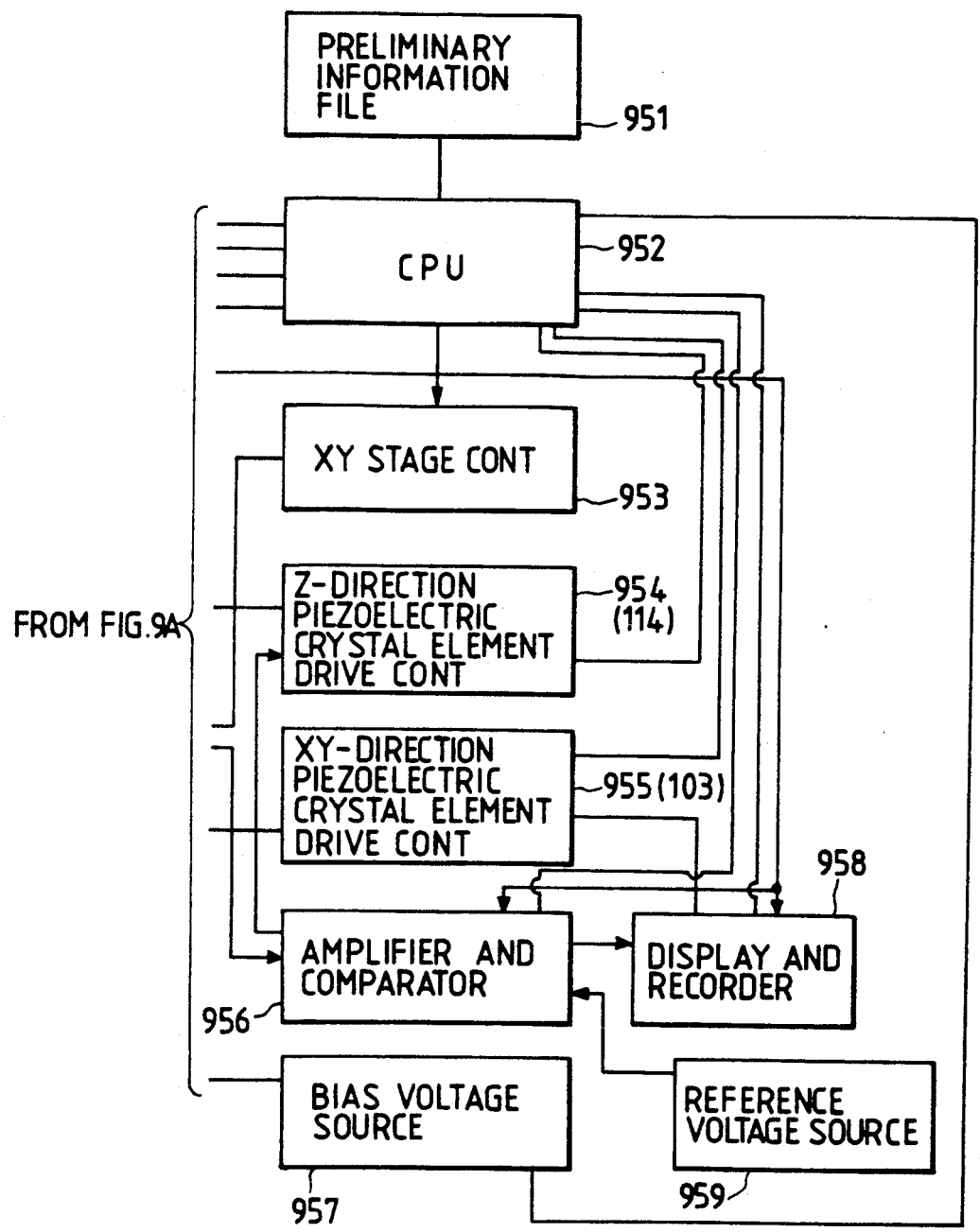
FIG. 9(A–C) are a schematic view showing an embodiment of a minute portion processing apparatus or a minute portion analyzing apparatus of the present invention.

FIG. 9 shows an example of a system for detecting, correcting, or analyzing a device element relating to the present invention. The equipment is placed on a vibration-proof table 901. A main unit 902 of a NOSM and-/or a STM is installed in a vacuum chamber 900 which is evacuated highly or ultra-highly by an exhaust system such as a turbo-molecular pump 902b or an ion pump 902c, and a laminated vibration-proof rubber sheet 903 or a spring is used for preventing vibration. An XY stage is mounted on a vibration-proof plate 904 comprising laminated rubber and driven by a drive motor 906. A specimen 101 is attached to a holder 909 on a loading mechanism installed in a load chamber 908. The load chamber 908 is evacuated by a rotary pump 911, and the above holder 909 is transported to an XY stage 913 which is moved to the P position with a gate valve 912 open. The gate valve 912 is closed thereafter, the XY stage 913 is moved to the Q position, and the operation such as detection, processing, or analazing is performed. In this case, it is required to stop pumps, which generate vibration, such as the rotary pump 911 and the turbo-molecular pump 902b for rough evacuation.

On the basis of a preliminary information file 951 for design data and field test data, a CPU 952 issues an instruction to an XY stage control system 953 so as to move the XY stage 913 so that the area of the specimen 101 requiring detection, correction, or analysis comes almost right under a NOSM tip and/or a STM tip 107. In this case, the distance of a mirror 922 on the XY stage 913 can be measured with high accuracy by a laser length measuring machine 917 through a polarizing prism 918 and a window 919 of the vacuum chamber. A SEM 915 is installed so that the vicinity comes in sight. A SEM controller 915a observes the tip 107 and the specimen 101 as SEM images, and their positions can be checked and adjusted more accurately. From data of SEM images from the SEM controller 915a, the CPU 952 can position the desired minute portion using the target mark, pattern, foreign particle, stain, scratch, or defect on the specimen 101 as a mark.

Although not described in detail in the drawing, a drive mechanism 916 of the STM tip and/or NOSM tip 107 in the Z direction comprises a rough mechanism 113 with a long stroke and a highly accurate piezoelectric drive mechanism 112. When the SEM controller 915a connected to the SEM 915 is observing the tip 107 and the specimen 101 as SEM images, the above rough mechanism 113 allows the tip 107 to approach (move to) the specimen 101 and the piezoelectric drive mechanism 916 in the Z direction adjusts the position finely. The detected quantity of the reflected light from the specimen 101 which passes through the NOSM tip and/or STM tip 107 and the detected value of the tunnel current are calculated from an amplifier and comparator 956 and the CPU 952 adjusts the distance between the tip 107 and the specimen 101 with high accuracy.

As to the SEM, a bias voltage is applied to the NOSM or STM tip 107 by a bias power source 957, the current flowing between the tip 107 and the specimen 101 is amplified by the amplifier and comparator 956, and compared with the output of a reference voltage source 959 which is fixed beforehand. The difference is amplified and supplied to a drive controller 954 of the piezoelectric element in the Z direction so as to drive the piezoelectric element in the Z direction, and the distance between the specimen surface and the tip can be kept at a predetermined fixed value with high accuracy. A piezoelectric element 920 in the XY direction is driven by a drive controller 955 of the piezoelectric element in the XY direction, the specimen is scanned in the XY direction by an XY scanner 102, and the corresponding drive voltage in the Z direction is displayed on the display. By doing this, the resolution ranging from nm to the atomic size can be displayed on a display and recorder 958. A method that the specimen 101 is driven in the XY direction with the height in the Z direction kept constant and an obtained change in the tunnel current is displayed on the display 958 can be used.

Next, the output of a laser resonator 109 driven by a laser resonator power controller 960 passes through an intermediate optical system 111 controlled by an intermediate optical system controller 963, passes through a window 965 of the vacuum chamber 900, and is reflected off of a half mirror 805, focused by an objective lens 108, and irradiated to a minute area on the specimen surface by the NOSM tip 107. The reflected light from the specimen 101 passes through the NOSM tip 107, then passes through the objective lens 108, the half mirror 805, and the window 969 of the vacuum chamber, and is detected by a detector 116 and amplified by an amplifier 971. Since the reflectivity of the specimen 101 is almost constant at any location, the output of the reflected light is amplified by the amplifier and comparator 956 and compared with the voltage of the reference voltage source 959 which is preset. The difference is supplied to the drive power source 954 of the piezoelectric element in the Z direction so as to keep the distance between the specimen 101 and the NOSM tip 107 in the Z direction almost constant.

By doing this, a STM image or a NOSM image is detected by the STM tip 502 or the NOSM tip 107, a high resolution image at a necessary location is obtained with reference to the data file, which is stored in the preliminary information file 951 once again, or other data such as SEM images, and a minute portion in the desired range from 20 nm to the atomic size can be detected, processed, annealed, or analyzed by the STM, STS, or NOSM.

The equipment shown in FIG. 9 is equipped with a mechanism for charging gas around the specimen. Gases which can be used are as follows:

(1) Gases for chemical vapor deposition (CVD) of a metal
  (a) Alkyl metal: $M(C_nH_{2n+1})_m$, for example, $Al(CH_3)_3$, $Al(C_2H_5)_3$, $Al(C_4H_9)_3$, $Cd(CH_3)$, $Cd(C_2H_5)_2$
  (b) Metal carbonyl: $M(CO)_n$, for example, $Mn(CO)_6$, $W(CO)_6$
  (c) Metal alkoxide: $M(OC_nH_{2n+1})_m$, for example, $Ta(OC_2H_5)_5$
  (d) Metal halide: MX, for example, $WF_6$, $WCl_6$
(2) Gases for CVD of oxide film or nitride film TEOS (Tetra etoxy silane), DES (Diethyl silane), oxidizing gas, nitriding gas, $O_2$, $N_2O_2$, $H_2O_2$
(3) Gases for CVD of semiconductor materials or impurity materials $SiH_4$, $A_6H_3$, $PH_3$, $Ga(CH_3)$, $Ga(C_2H_5)_3$, In $(CH_3)_3$, $H_2Se$, $H_2S$, $Zn(C_2H_5)_2$
(4) Assist gases for dry etching $F_2$, $Cl_2$, XeF, ArF One of these gases, which is gaseous at normal temperature, for example, $F_2$ or $Cl_2$ is taken out from a cylinder 980 via a valve 984. In this case, the above gas can be mixed with dilution gas separately contained in a cylinder 983 by a gas mixer 990. A solid, which is sublimed at normal temperature, for example, $Mo(CO)_6$ is sublimed in a box 987 beforehand. In this case, a heater 989 mounted to the box 987 can be used so as to accelerate sublimation by heating. Carrier gas contained in a cylinder 981 is fed to the cylinder 987 via a valve 984 so as to transport gas from the solid. Furthermore, a liquid, which is liquefied at normal temperature, for example, trymethylaluminum $Al(CH_3)_3$ is supplied into a bubbling container 988 from a cylinder 982 via a valve 984 and bubbled by carrier gas such as $N_2$, which is separately fed, so as to allow a part of the liquid material to be dissolved in the carrier gas as vapor. The dissolved gas is transported with the carrier gas.

These gases can be used independently or a plurality of gases can be mixed by the mixer 990 before starting use. Finally, these gases are supplied to the vacuum chamber 900 via a flow regulating valve 991 and ejected to the specimen 101 and its vicinity from a gas guide nozzle 992 mounted to the lens tube of the SEM 915.

In FIG. 9, the intermediate optical system 111 can be used together with various optical systems shown below when necessary.

Figure 10:
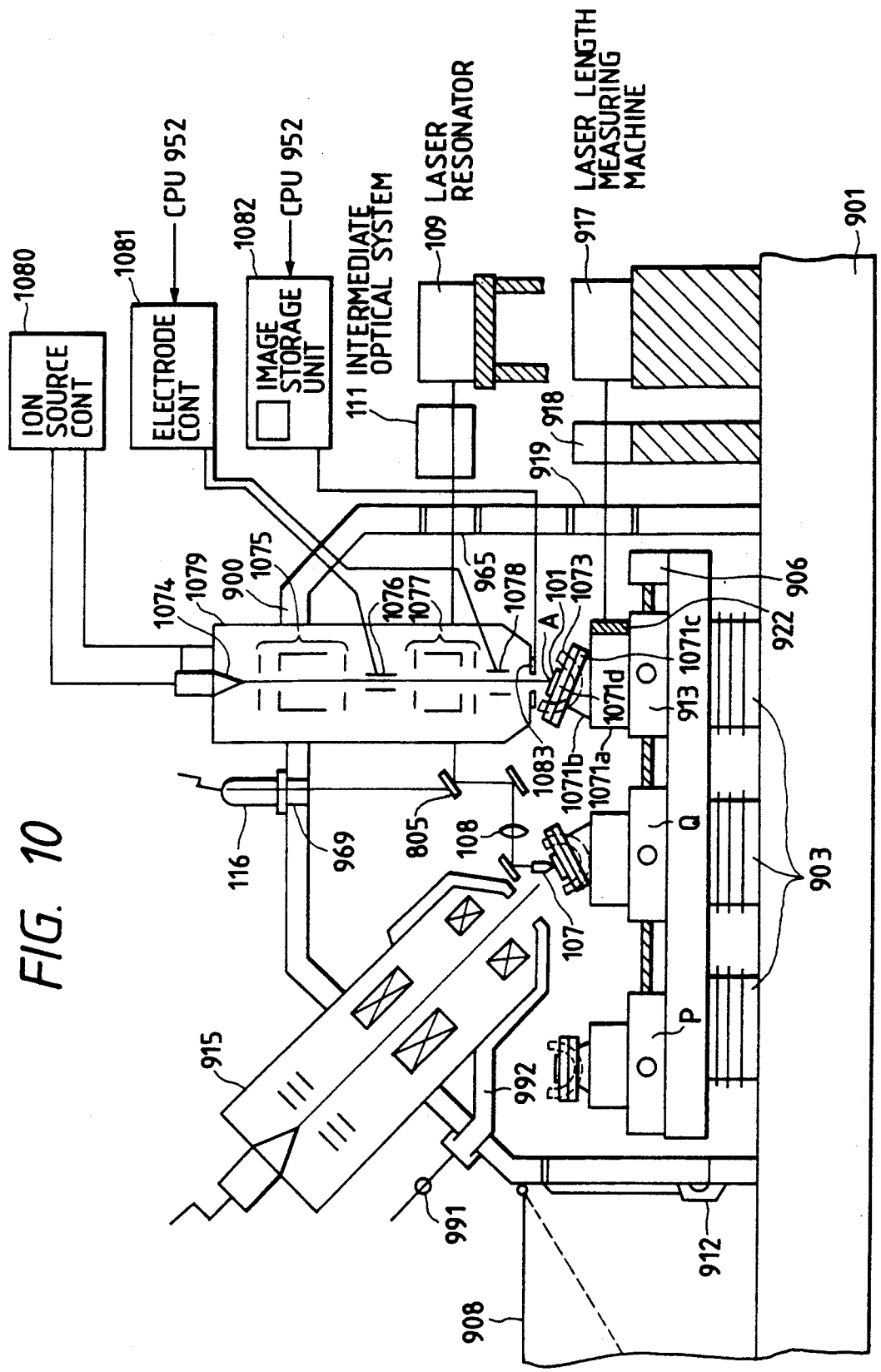
FIG. 10 is a schematic view showing an embodiment of a minute portion processing apparatus or a minute portion analyzing apparatus of the present invention which is different from the embodiment shown in FIG. 9.

(1) Lenses and mirrors for adjusting the optical axis direction or the beam diameter
(2) A polarizing filter or polarizer for fixing or changing the polarizing direction of a ND filter for adjusting the intensity
(3) A wave length selection filter for selecting a special wave length from a multi-wave laser such as an ion laser or from a laser with a wide wave length zone such as a dye laser
(4) An optical system for reducing the coherence of the laser resonator used
(5) Others FIG. 10 shows an embodiment wherein a focused ion beam-processing system (FIB apparatus), a tilt mechanism of the specimen stage, and a tilt mechanism of the NOSM and/or STM tip are added to the equipment shown in FIG. 9.

A focused ion beam column 1079 other than the one shown in FIG. 9 may be used as a vacuum chamber 900. The column focuses an ion beam from a high-intensity ion source 1074 such as a liquid-metal ion source by electrostatic lenses 1075 and 1077 to a narrow beam and irradiates it to the specimen 101. Particularly by using a combination of the first electrostatic lens 1075 and the second electrostatic lens 1077, the ion beam can be focused to a spot 60 nm to 30 nm in diameter on the specimen surface.

Numeral 1076 indicates an eight-pole electrode serving as an anastigmat and a deflector, which corrects the astigmatism of the beam or polarizes the beam. Numeral 1078 indicates a deflector electrode, which polarizes the beam together with the eight-pole electrode 1076. A minutely focused ion beam can be sputtered by irradiating it to an extremely narrow area.

By detecting secondary electrons or secondary ions generated from an irradiated specimen by a secondary charged particle detector 1083 such as a channel plate, a specimen image which is similar to a SEM image or an image of scanning ion microscopy (SIM image) can be obtained.

In this case, the processing is progressed simultaneously with observation. Therefore, by minimizing the scanning count for observation by storing images in an image storage unit 1082 by one scanning, images for processing during observation can be minimized. Numeral 1080 indicates an ion source controller and 1081 an electrode controller which is connected to a CPU 952. The image storage unit 1082 is also connected to the CPU 952.

The tilt mechanism of the specimen stage is a concentric tilt mechanism which minimizes the displacement of the beam caused by the rotation whose center is the position where the beam is irradiated. The tilt mechanism comprises a mount 1071c, whereto a gear 1073 is mounted, and a stage 1071d which are installed on the XY stage 913 using supports 1071a and 1071b. The gear 1073 rotates round an axis perpendicular to the paper, where FIG. 10 is drawn, centering at the beam irradiation point A on the specimen 101 according to a signal from the controller 955 (shown in FIG. 9) and the power by a vacuum motor, and can stop at an optional angle. By doing this, it is possible to observe an image or irradiate a beam at an optional angle. Even when the XY stage 913 moves to the position Q of the NOSM and/or STM tip and the SEM, it rotates by the tilt mechanism and can be opposite to the SEM or the NOSM and/or STM tip at an optional angle. When the specimen is to be exchanged at the specimen exchange position P, the specimen table 105 is required to be horizontal. It is desirable to indicate the stage, mount, uniaxial stage, or specimen, which is at the position Q or P, with broken lines. However, solid lines are used so that the units can be clearly recognized.

The specimen table 105 is required to be horizontal. In FIG. 10, the support 1071d is a uniaxial stage which can move on the amount 1071c fixed to the gear 1073 so as to move the specimen 101. Even when the support 1071d moves, the height of the ion beam irradiation position is left unchanged, and there is no need to change the beam focus when the stage 1071d moves or the gear 1073 rotates.

Figure 11:
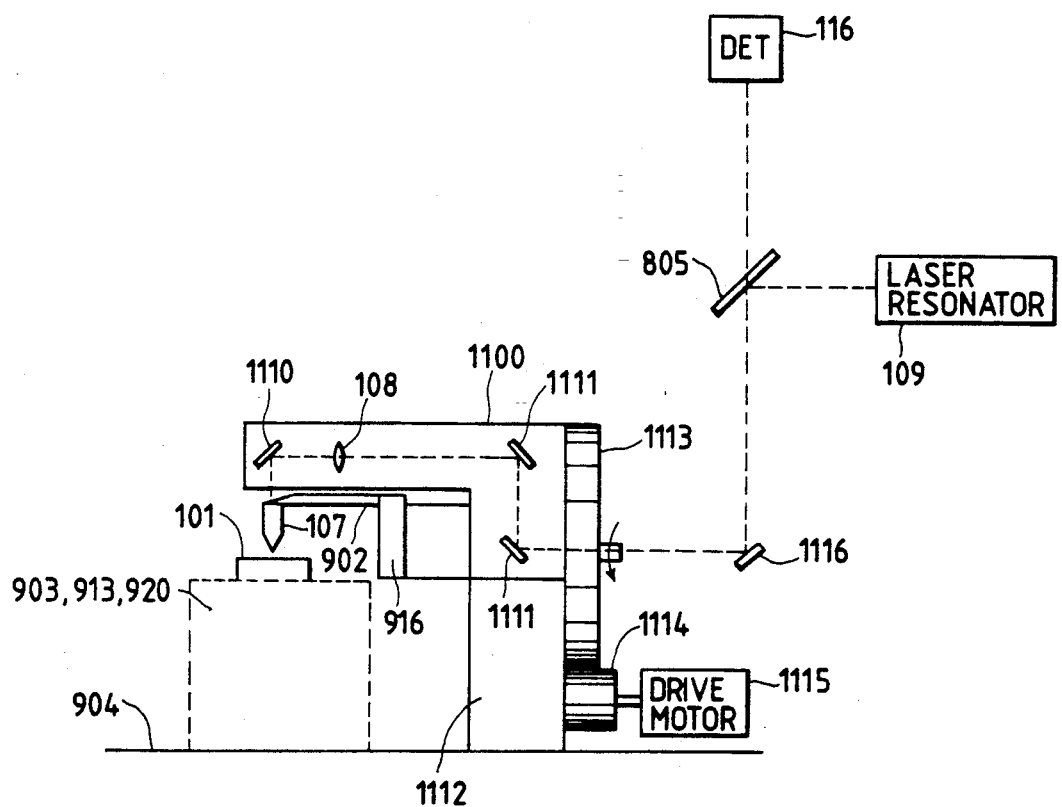
FIG. 11 is a drawing showing an embodiment that a tip and an optical system rotate.

The NOSM and/or STM tip shown in FIG. 10 is characterized in that the tip has a mechanism that it rotates round the end point of the tip. The mechanism will be described in detail hereunder. As shown in FIG. 11, a lens tube 1100, which has a rotation axis located at the same level as the surface of the specimen 101 and is supported so that it can freely rotate, is installed on a base 1112 mounted on the vibration-proof plate 904. A gear 1113 is mounted on the side of said lens tube 1100, and a gear 1114, which is engaged with the gear 1113, is mounted to the output axis of a drive motor 1115. The main unit 902 of the NOSM and/or STM having the NOSM and/or STM tip 107 and 502 is mounted at the tip of the above lens tube 1100. The main unit 902 of the NOSM and/or STM has a drive mechanism 916 (112, 113) comprising a combination of a rough mechanism 113 with a long stroke and a piezoelectric drive mechanism 112 with high precision in the Z direction. The lens tube 1100 comprises a mirror 1110, a lens 108, and two mirrors 1111. A half mirror 805 is positioned at the center of the rotation axis of the lens tube 1100 via a mirror 1116. A fixing means for fixing the lens tube 1100 to the base 1112, that is, the vibration-proof plate 904 after rotating the lens tube 1100 so as to control the rotation of the NOSM and/or STM tip 107 and 502, which is not shown in the drawing, is provided.

Next, the technique, which is applied to the above embodiment, will be described. FIGS. 12(a) and 12(b) and FIG. 13 show the atom configuration of the (111) surface of Si, and the correct (7×7) structure has been made clear by the STM for the first time. FIGS. 12(a) and 12(b) show the atom configuration which is cut from the front, and FIG. 13 shows a sectional view on the line AB. The so-called reconstructed layer near the surface comprises dimers (Z corpus quantum), stacking faults, and absorption atoms. The atom configuration of the dimer layer is almost the same as that of the (111) lattice plane of crystal, and three dimers are formed along each side of two triangles of sub-unit cells. Each angle contains a vacancy of atom. The dimer gap is longer than the general Si—Si bond length by 9%. Si atoms of the stacking fault layer are at the C position in the sub-unit cell on the left and at the B position on the right.

As to absorption atoms, there are six absorption atoms in a sub-unit cell and their positions are fixed. Absorption atoms can be separated and read by the STM so as to configure an extremely high density memory device. As shown in FIG. 12(b), for example, a diamond-shaped cell (unit cell) can be expressed by polar coordinates (m,n) using symbols m and n which indicate the numbers of cells on the axes, which intersect at 60°, between the cell and the same reference point O. One unit cell contains 12 absorption atoms. By determining the coordinates as 1, 2, and 3 in the P axis direction and 1, 2, and 3 in the Q axis direction sequentially starting at the lower left vertex in the lower left sub-unit cell and by determining the coordinates as $\bar{1}, \bar{2},$ and $\bar{3}$ in the P axis direction and $\bar{1}, \bar{2},$ and $\bar{3}$ in the Q axis direction sequentially starting at the upper right vertex in the upper right sub-unit cell, all absorption atoms can be specified by (i,j) ($|i|\leq 3, |j|\leq 3, |i+j|\div 4$). Therefore, every absorption atom on the Si surface of the (7×7) structure of a perfect (111) plane can be specified by (m,n,i,j) (m, n, i, and j are integers except 0, and $|i|\leq 3, |j|\leq 3, |i+j|\leq 4$.

The needle tip of the STM approaches the Si surface as shown in FIG. 13 and keeps a predetermined distance of $\delta$ to the absorption atom $H_1$ at the particular coordinates ($m_1, n_1, i_1, j_1$) by detecting an image and tunnel current, and then advances by a predetermined distance of $\delta'$ in the Z direction. By doing this, a hole is formed at the location of the $H_1$ atom by plastic deformation. Next, the needle tip is pulled up, and then moves to the next position ($m_2, n_2, i_2, j_2$), keeps the predetermined distance $\delta$ to the $H_2$ atom by detecting the tunnel current in the same way, and then advances by the predetermined distance $\delta'$ in the Z direction so as to form a hole at the location of the $H_2$ atom. By repeating this operation, a hole can be formed at the location of the absorption atom $H_k$ at the particular coordinates ($m_k, n_k, i_k, j_k$) so as to create a ROM (read only memory).

A method that the needle approaches to a predetermined distance from the atom $H_k$, the tunnel current is increased by increasing the applied voltage, and the absorption atom is given large energy and separated from the Si surface may be used. Since the absorption atom is not subject to plastic deformation in this case, a method that $SiH_4$ is reversely decomposed and Si is deposited may be used for separating the absorption atom and giving a Si atom in the hole.

By this method, a RAM (random access memory) for writing or erasing data in or from the (111) surface of Si can be configured.

Furthermore, by flowing a tunnel current in a reactive gas ($F_2$, $Cl_2$, etc.), Si atoms can be changed to stomatal materials, volatilized, and eliminated.

The technique mentioned above uses the atom configuration (7×7) of the (111) surface of Si as a memory device. An optional crystal face such as Si (110) may be used instead of Si (111), and the technique may be used for another element or molecule configuration.

FIGS. 14(a) to 14(e) show embodiments of another memory device. A LB film (Langumuir-Blodgett's film) is formed on a substrate, for example, a glass substrate or a Si substrate. As shown in FIG. 15(a), for example, a glass substrate is subjected to the hydrophobic processing by $(CH_3)_3SiOH$, and as shown in FIGS. 15(b) and 15(c), a LB film is formed on the glass substrate using a long chain compound such as carboxylic acid or carboxylic acid alkali.

Figure 14A:
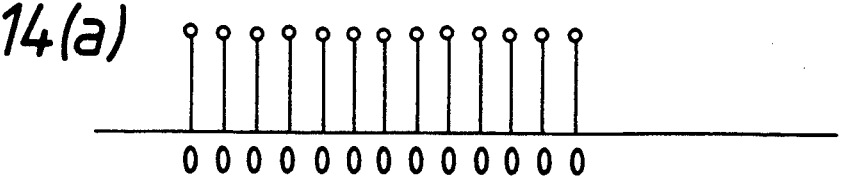
Figure 14B:
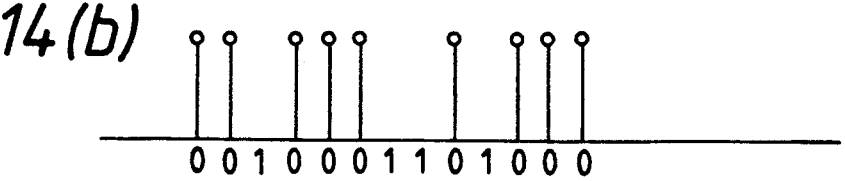
Figure 14C:
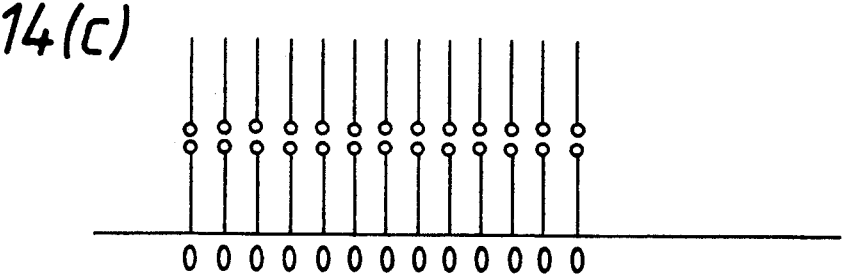
Figure 14D:
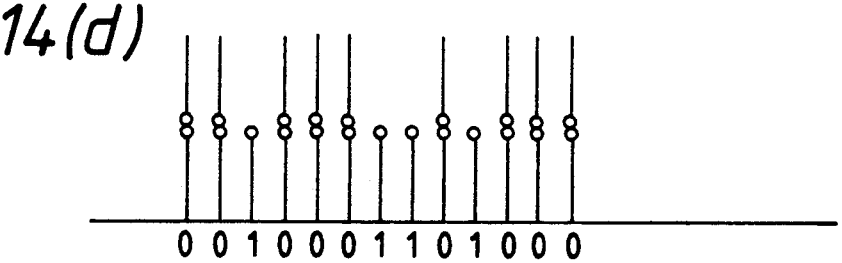
Figure 14E:
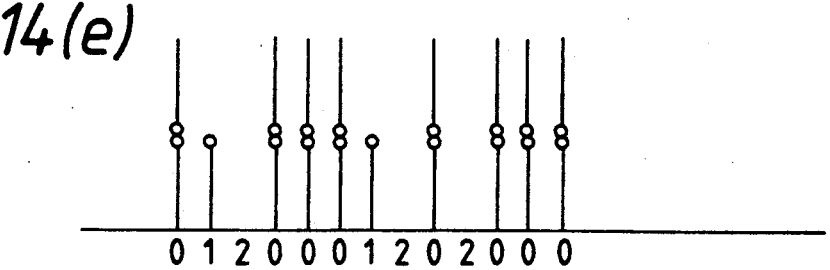

When one LB film is formed, $(CH_2)_nCOOH$ is uniformly bonded to a layer as shown in FIG. 14(a). It is assumed that 1 bit is allocated to each molecule and the bits are all 0. The STM detects the molecules one by one, and a large STM current is flowed in a molecule at a specified location so as to dissociate the bond with the substrate and eliminate the molecule. This state is assumed as 1. By doing this, data is written into the memory as shown in FIG. 14(b). This reading is performed by the STM in the same way. FIGS. 14(a) to 14(e) show sectional views, though the molecules are spread on a two-dimensional plane. In FIG. 14(c), two LB films are formed. In this case, $(CH_2)_nCOOH$ and $HOOC(CH_2)_n$ are hydrophilic radicals and hydrogen-bonded. By flowing a large current in a $HOOC(CH_2)_n$ molecule at a specified location by detection of the STM, the hydrogen bonded section can be separated so as to eliminate the upper layer of $HOOC(CH_2)_n$. FIG. 14(e) shows an example that the memory device is used as a multi-value memory. By using a method that a current, which flows in $(CH_2)_nCOOH-HOOC(CH_2)_n$ at a specified location by the STM tip, changes in magnitude depending on an change in the applied voltage, the bond between the upper layer of molecules and the lower layer of molecules is dissociated, and whether or not to separate the bond between the lower layer of molecules and the substrate can be selected. By allocating 0, 1, or 2 to each bit on the assumption that the former is 1 and the latter is 2, a three-value memory can be configured.

FIG. 16 shows an example that a memory device is configured by allocating a bit to 5 molecules (5×5=25 molecules on a plane). Light is irradiated to specified molecules in bit units by the NOSM, those molecules are eliminated by melting evaporation or photo-chemical dissolution, and data is recorded as shown in FIG. 16(a). In FIG. 16(b), the above multi-value memory is used. Although 1 bit is allocated to 5×5=25 molecules in the same way, two LB films are used and 1 or 2 is written by selecting whether only the molecules on the upper film are subject to melting evaporation by controlling the intensity of the light which is irradiated by the NOSM or the molecules on the lower film are also subject to melting evaporation. O is indicated at locations where nothing is eliminated in the same way. By measuring the height by the STM or detecting the intensity of the transmitted light or the reflected light or spectrums by the NOSM, the value 0, 1, or 2 of each bit can be read.

The bond can be dissociated selectively by changing the light wave length instead of the above technique for changing the light intensity. By selecting a specified wave length from the output of a multi-wave argon laser or the output of a dye laser with a wide spectrum width using a wave length selection filter by Fabry-Pverot etalon or an absorption wave length selection filter and selecting whether the bond between the molecules on the upper layer of the two-layer molecular structure and the molecules on the lower layer is to be dissociated or the bond between the molecules on the lower layer and the substrate is to be dissociated, 1 or 2 can be written.

As described above, the present invention obtains good results that a minute portion ranging from 20 nm to the atomic size can be detected, processed, film-formed, annealed, or ion-implanted, atoms or molecules can be removed or inserted, or foreign particles or defects can be analyzed.

Furthermore, the present invention obtains good results that a ROM or RAM can be directly configured and data can be written in or erased from a memory device.

Furthermore, the present invention obtains good results that defects including foreign particles of 20 nm or less existing on the surface or in the interior of a wafer or device element can be detected or analyzed.

Next, the first embodiment of a photoacoustic signal detection apparatus whereto the present invention is applied will be described with reference to FIGS. 17 to 20. FIG. 17 shows a photoacoustic detection optical system of the first embodiment of a photoacoustic signal detection apparatus. The optical system comprises an exciting-light optical system 110, a detection system 120, and a signal processing system 130. The optical system uses a near-field optical scanning microscope (hereinafter abbreviated to NOSM) as a specimen exciting means and a scanning tunneling microscope, which is combined with the above NOSM, as a means for detecting a minute displacement of the specimen surface caused by the photoacoustic effect. The exciting-light optical system 110 modulates the intensity of parallel light irradiated from a laser 31 at a predetermined frequency by an acousto-optical modulation element 32, enlarges the intermittent light to a desired beam diameter by a beam expander 33, focuses it by a lens 35, and sends it to a NOSM tip 36c.

Figure 18A:
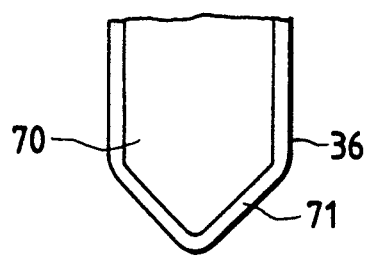
Figure 18B:
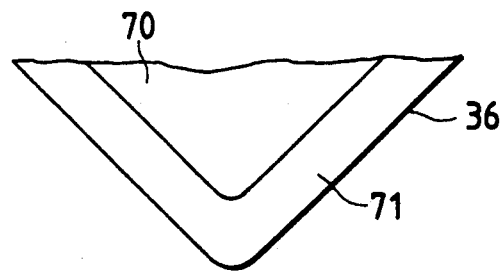

The intensity modulation frequency of the above laser beam is set so that the thermal diffusion length in a specimen is equal to or smaller than the optical spot diameter on the specimen. Next, the NOSM tip 36c will be described. As shown in FIG. 18(a) and FIG. 18(b) (an enlarge view of the tip), the surface of a quartz glass rod 70 with a tip polished sharply to about 10 nm is deposited with a highly conductive metal thin film 71. When the quartz glass rod is pressed against a flat surface 72, deposited metal 71a at the tip is spread flatwise on the flat surface 72, the deposited metal film 71a at the tip 105 of the glass rod 70 becomes thinner than the so-called skin depth or is removed, causing the glass rod to be exposed. This area is called an aperture. When light is irradiated from above the glass rod, the light can pass through an extremely narrow area (aperture) of the tip. By doing this, a NOSM tip comprising a sharp tip, an aperture formed at the tip, and an opaque coating around the aperture is formed. In other words, the NOSM tip 36a is a needle-shaped light transmission body which is formed so that light passes through only an extremely narrow area of about 10 nm of the tip.

The NOSM tip may be different from the one shown in FIGS. 18(a) to 2(c). Another example that a narrow hollow glass tube is melted, lengthened, and cut into pieces is available (not shown in the drawing). In this case, a narrow aperture of about 10 nm can be produced. By depositing a metal thin film on the surface of the hollow glass tube, a NOSM tip 107 can be formed.

Figure 18C:
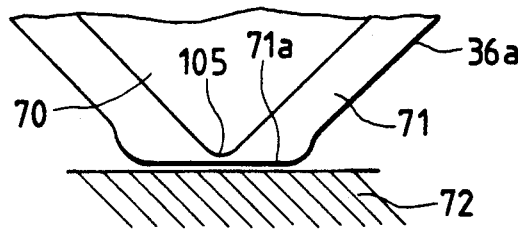
Figure 18D:
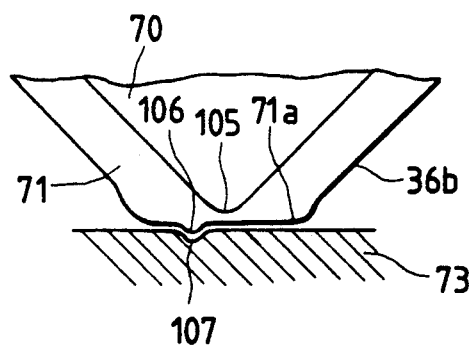
Figure 18E:
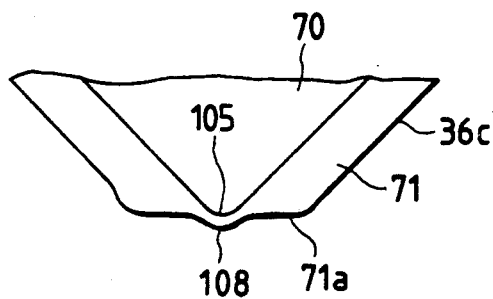
Figure 18F:
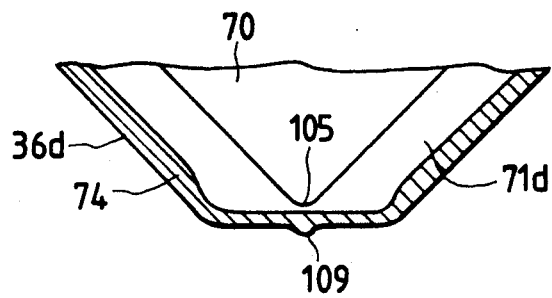

In the first embodiment of a photoacoustic detection apparatus, the above NOSM tip can be used as a tunnel current detection tip. As shown in FIG. 18(d), by pressing the metal thin film 71a at the tip 105 of the glass rod 70, whereto the metal thin film 71 is deposited, against a flat surface 73 having a minute hollow 107 so as to spread the metal thin film 71a, a minute protrusion 106 for tunnel current detection can be formed on the metal thin film 71a at the tip of the rod. By irradiating a laser beam, for example, locally and applying a high voltage to the formed flat section 71a as shown in FIG. 18(c), a minute protrusion 108 can be formed as shown in FIG. 18(e). FIG. 18(e) shows an example that a minute protrusion is formed at the position of the aperture by this method. In this case, there is an advantage that the gap between the aperture and the specimen can be detected immediately by a tunnel current. As shown in FIG. 18(f), a transparent conductive layer 74, for example, $SnO_2$ or $In_2O_3$ is deposited on the surface of the NOSM tip shown in FIG. 18(c), and pressed against the flat surface 73 with the hollow 107 so as to spread. By doing this, a minute protrusion 109 can be formed at the position of the tip 105. There is an advantage that since the tip 36d uses a transparent conductive layer, variations in the wave front at the protrusion can be minimized. Particularly, when the refractive index of the transparent conductive layer 74 is made equal to that of the atmosphere between the NOSM tip 36d and the specimen 7, for example, air, variations in the above wave front can be minimized, and the effect of the minute protrusion 109 on the light behavior can be almost eliminated.

In the first embodiment of a photoacoustic signal detection apparatus, the tip 36c shown in FIG. 18(e) is used as a NOSM tip which can be used for tunnel current detection as described above. In FIG. 1, the gap between the aperture 105 of the NOSM tip 36c and the specimen 7 is close to the size of the aperture. The light, which passes through the aperture 105 of the NOSM tip 36c, forms a minute optical spot of about 10 nm on the surface 104 of the specimen 7. This minute optical spot generates elastic heat waves (ultrasonic waves) in the specimen on the basis of the photoacoustic effect and a minute displacement on the surface of the specimen 7 simultaneously.

When the atoms at the tip of the minute protrusion of the NOSM tip 36c of the detection system 120 approach the atoms of the surface of the specimen 7 and the distance becomes about 2 nm, a tunnel current starts flowing by application of several volts. The NOSM tip 36c approaches the specimen 7 by the piezoelectric element 39 and the actuator 38 by applying several volts between the metal deposited film 71 of the NOSM tip 36c and the specimen 7 from a voltage source 51 and stops approaching when a tunnel current is detected.

A tunnel current $I_t$ flowing when there is a potential difference of V between a NOSM tip, which is at a distance of Z from the surface of a specimen of a work function $\phi$, and the specimen surface is expressed by the foregoing equation (3). Therefore, by detecting a change in the tunnel current $I_t$, a minute displacement of the surface of the specimen 7 caused by the photoacoustic effect can be detected.

The detected tunnel current $I_t$ is amplified by a current-voltage converter 41 and a logarithmic amplifier 52. In this embodiment, a signal switching unit 42 is connected to a terminal A as shown in FIG. 17. A tunnel current detection signal is sent to a lock-in amplifier 43 of the signal processing system 130. In the lock-in amplifier 43, the amplitude of the modulation frequency component contained in the tunnel current detection signal and the phase component for a modulation signal from an oscillator 40, which is used for driving an acoustic-optical modulation element 32, are extracted using the modulation signal as a reference signal. The frequency and phase component have information on a thermal diffusion area Vth which is determined by the modulation frequency. When a defect such as a crack or a minute portion with a different thermal impedance exists in the thermal diffusion area Vth 23, the frequency and phase of the modulation frequency component of the tunnel current detection signal are changed so as to indicate the presence of such a defect or minute portion.

The tunnel current detection signal outputted from the logarithmic amplifier 52 is sent to a comparator 46 simultaneously. The comparator 46 compares a reference signal sent from a CPU 44 with the detected tunnel current signal so as to keep the distance between the NOSM tip 36c and the specimen 7 constant, and sends the differential signal to a high-voltage amplifier 48 for driving the piezoelectric element 39 via a low-pass filter 47. The frequency characteristics of the low-pass filter 47 are as shown in FIG. 3. A symbol fs indicates a sampling frequency for sending an output signal from the lock-in amplifier to the CPU 44, fc a cut-off frequency of the low-pass filter and also the maximum drive frequency of the piezoelectric element 39, and $f_L$ the modulation frequency of an exciting laser 31. The low-pass filter does not follow a change in the tunnel current signal corresponding to a minute displacement of the surface of the specimen 7 caused by the photoacoustic effect, but follows changes in the distance between the NOSM tip 36c and the specimen 7 caused by irregularities of the specimen surface or thermal drifting for a comparatively long period of time during scanning of the specimen 7, sends a control signal for driving the piezoelectric element 39 to the high-voltage amplifier 48, and moves the NOSM tip 36c finely. As a result, the distance between the NOSM tip 36c and the specimen 7 can be kept constant always regardless of irregularities of the surface of the specimen 7 as shown in FIG. 20, a minute optical spot with a fixed diameter can be formed always on the specimen without being affected by irregularities of the specimen surface, and a photoacoustic signal can be stably detected always.

An XY stage 49 comprises a rough movement mechanism by a pulse motor and a fine movement mechanism by the piezoelectric element and can scan the specimen 7 in the x and y directions with accuracy of less than 1 nm. A Z stage 50 is used to roughly control the distance between the NOSM tip and specimen with accuracy of about 0.1 μm.

A position signal from the XY stage 49 and an output signal from the lock-in amplifier 43 are processed by the CPU 44, and a photoacoustic signal at each point on the specimen 7 or a two-dimensional photoacoustic image is outputted to a display 45 such as a monitor TV.

In this embodiment, as described above, a minute optical spot of about 10 nm is formed on the specimen surface by the NOSM and a minute displacement of the specimen surface on the basis of the photoacoustic effect in the specimen caused by this minute optical spot is detected as a change in a tunnel current flowing between the NOSM tip and specimen. In this embodiment, the specimen surface can be excited by a minute optical spot of about 10 nm because the NOSM is used as a specimen exciting means and the resolution of a photoacoustic signal in the transverse direction is extremely improved. Furthermore, by using a tunnel current for detecting the photoacoustic effect, a minute displacement in A units can be detected and the detection sensitivity is extremely improved. By setting the aperture of the NOSM tip and the tunnel current detection protrusion at the same location, the detection sensitivity and the signal-to-noise ratio are extremely improved. The detected tunnel current signal can be used as a control signal for the distance between the NOSM tip and specimen for a comparatively long period of time via the comparator and the low-pass filter. Therefore, a photoacoustic signal can be detected stably for an uneven specimen.

The second embodiment of a photoacoustic signal detection apparatus whereto the present invention is applied will be described with reference to FIG. 17. In this embodiment, the configuration of the photoacoustic signal detection system is the same as that of the first embodiment shown in FIG. 17. Therefore, it will not be described hereunder. In this embodiment, the signal switching unit 42 is connected to the terminal B. In FIG. 17, the detected tunnel current signal is sent to the comparator 46, and a control signal for keeping the tunnel current between the NOSM tip 36c and the specimen 7 constant is sent to the lock-in amplifier 43 and simultaneously to the high-voltage amplifier 47 for driving the piezoelectric element 39 via the low-pass filter 47.

In this embodiment, this control signal is used as a signal for detecting a minute displacement of the surface of the specimen 7 caused by the photoacoustic effect. The modulation frequency $f_L$ of the laser 31 is required to be set to a value so that the piezoelectric element 39 can be controlled. As shown in FIG. 21, the modulation frequency is set to a value smaller than the cut-off frequency fc (this value is equal to the maximum drive frequency of the piezoelectric element 39) of the low-pass filter 47 and larger than the sampling frequency fs of the lock-in amplifier output signal. The processing of the lock-in amplifier 43 and subsequent units is the same as that of the first embodiment, and finally a two-dimensional photoacoustic image is outputted to the display 45 such as a monitor TV.

This embodiment can obtain good results equal to those of the first embodiment though the modulation frequency is limited to an extent.

The third embodiment of a photoacoustic signal detection apparatus whereto the present invention is applied will be described with reference to FIGS. 22 and 23. FIG. 22 shows a photoacoustic signal detection system of the third embodiment of a photoacoustic signal detection apparatus. The optical system comprises an exciting-light optical system 210, a detection system 220, and a signal processing system 230. The optical system uses a NOSM as a specimen exciting means and also the NOSM as a means for detecting a minute displacement of the specimen surface caused by the photoacoustic effect.

The exciting-light optical system 210 modulates the intensity of parallel light irradiated from a laser 31 at a predetermined frequency by an acoustic-optical modulation element 32, enlarges the intermittent light to a desired beam diameter by a beam expander 33, allows it to reflect off of a dichroic mirror 80, focuses it by a lens 35, and sends it to a NOSM tip 36c. The NOSM tip type is required to be the one shown in FIG. 18(c). The gap between the aperture 105 of the NOSM tip 36a and the specimen 7 is close to the size of the aperture. The light, which passes through the aperture 105 of the NOSM tip 36a, forms a minute optical spot of about 10 nm on the surface 104 of the specimen 7. This minute optical spot generates elastic heat waves (ultrasonic waves) in the specimen on the basis of the photoacoustic effect and a minute displacement on the surface of the specimen 7 simultaneously.

There is a fixed relationship shown in FIG. 23 between the distance Z between the NOSM tip 36a and the specimen 7 and the light quantity E passing through the aperture 105 of the NOSM tip 36a. Symbols A, B, and C indicate a proximity area, a near-field area, and a far-field area, respectively. The inclination of the linear section in the near-field area B is about −3.7. Therefore, by observing a change in the quantity of the reflected light from the specimen surface which passes through the aperture 105 of the NOSM tip 36a, a change in the distance Z between the NOSM tip 36a and the specimen 7 or a minute displacement of the surface of the specimen 7 caused by the photoacoustic effect can be detected. The quantity of the reflected light is detected by the detection system 220 which is described below.

The detection system 220 enlarges parallel light irradiated from a laser 81, which is different in wave length from the laser 31, to a desired beam diameter by a beam expander 82, allows it to reflect off of a beam splitter 83, allows it to pass through the dichroic mirror 80, focuses it by the lens 35, and sends it to the NOSM tip 36a. In the same way as with the exciting-light optical system 210, the light, which passes through the aperture 105 of the NOSM tip 36a, forms a minute optical spot of about 10 nm on the surface 104 of the specimen 7. The reflected light passes through the aperture 105 of the NOSM tip 36a once again and is changed to parallel light by the lens 35. The parallel light passes through the dichroic mirror 80 and the beam splitter 83, focuses to a back focal point 115 by a lens 84, and is detected by a photoelectric conversion element 86 such as a photodiode. A pin hole 85 is installed at the back focal point 115 so as to shield stray light or interference components generated in the lens 35 or 84 5 or in the NOSM tip 36a, or high-order diffracted light components generated by minute irregularities of the specimen surface.

The reflected light detection signal, which is photoelectrically converted, is amplified by a preamplifier 87 and a logarithmic amplifier 52. In this embodiment, a signal switching unit 42 is connected to a terminal A as shown in FIG. 22. The amplified reflected light detection signal is sent to a lock-in amplifier 43 of the signal processing system 230. In the lock-in amplifier 43, the amplitude of the modulation frequency component contained in the reflected light detection signal and the phase component for a modulation signal from an oscillator 40, which is used for driving an acoustic-optical modulation element 32, are detected using the modulation signal as a reference signal. The frequency and phase component have information on a thermal diffusion area Vth which is determined by the modulation frequency. When a defect such as a crack or a minute portion with a different thermal impedance exists in the thermal diffusion area Vth 23, the frequency and phase of the modulation frequency component of the reflected light detection signal are changed so as to indicate the presence of such a defect or minute portion.

This reflected light detection signal is sent to a comparator 46 simultaneously. The comparator 46 compares a reference signal sent from a CPU 44 with the detected reflected light signal so as to keep the distance between the NOSM tip 36a and the specimen 7 constant, and sends the differential signal to a high-voltage amplifier 48 for driving the piezoelectric element 39 via a low-pass filter 47. The frequency characteristics of the low-pass filter 47 are as shown in FIG. 19 in the same way as with the first embodiment. The low-pass filter does not follow a change in the reflected light signal (this change corresponds to a change in the modulation frequency $f_L$) corresponding to a minute displacement of the surface of the specimen 7 caused by the photoacoustic effect, but follows changes in the distance between the NOSM tip 36a and the specimen 7 caused by irregularities of the specimen surface or thermal drifting for a comparatively long period of time during scanning of the specimen 7, sends a control signal for driving the piezoelectric element 39 to the high-voltage amplifier 48, and moves the NOSM tip 36a finely. As a result, the distance between the NOSM tip 36a and the specimen 7 can be kept constant always regardless of irregularities of the surface of the specimen 7 as shown in FIG. 20 in the same way as with the first embodiment, a minute optical spot with a fixed diameter can be formed always on the specimen without being affected by irregularities of the specimen surface, and a photoacoustic signal can be stably detected always. The configurations and functions of the XY stage 49 and Z stage 50 are the same as those of the first embodiment.

A position signal from the XY stage 49 and an output signal from the lock-in amplifier 43 are processed by the CPU 44, and a photoacoustic signal at each point on the specimen 7 or a two-dimensional photoacoustic image is outputted to a display 45 such as a monitor TV.

In this embodiment, as described above, a minute optical spot of about 10 nm is formed on the specimen surface by the NOSM and a minute displacement of the specimen surface on the basis of the photoacoustic effect in the specimen caused by this minute optical spot is detected as a change in the quantity of the reflected light passing through the NOSM tip. In this embodiment, the specimen surface can be excited by a minute optical spot of about 10 nm because the NOSM is used as a specimen exciting means and the resolution of a photoacoustic signal in the transverse direction is extremely improved. Furthermore, by using the quantity of the reflected light passing through the NOSM tip for detecting the photoacoustic effect, the detection sensitivity is extremely improved. The detected reflected light signal can be used as a control signal for the distance between the NOSM tip and specimen for a comparatively long period of time via the comparator and the low-pass filter. Therefore, a photoacoustic signal can be detected stably for an uneven specimen.

The fourth embodiment of a photoacoustic signal detection apparatus whereto the present invention is applied will be described with reference to FIG. 22. In this embodiment, the configuration of the photoacoustic signal detection system is the same as that of the third embodiment shown in FIG. 22. Therefore, it will not be described hereunder. In this embodiment, the signal switching unit 42 is connected to the terminal B. In FIG. 22, the detected reflected light signal is sent to the comparator 46, and a control signal for keeping the quantity of the reflected light constant or for keeping the distance between the NOSM tip 36a and the specimen constant is sent to the lock-in amplifier 43 and simultaneously to the high-voltage amplifier 48 for driving the piezoelectric element 39 via the low-pass filter 47. In this embodiment, this control signal is used as a signal for detecting a minute displacement of the surface of the specimen 7 caused by the photoacoustic effect. The modulation frequency $f_L$ of the laser 31 is required to be set to a value so that the piezoelectric element 39 can be controlled as shown in FIG. 21 in the same way as with the second embodiment. The processing of the lock-in amplifier 43 and subsequent units is the same as that of the third embodiment, and finally a two-dimensional photoacoustic image is outputted to the display 45 such as a monitor TV.

This embodiment can obtain good results equal to those of the third embodiment though the modulation frequency is limited to an extent.

The fifth embodiment of a photoacoustic signal detection apparatus whereto the present invention is applied will be described with reference to FIG. 24. FIG. 22 shows a photoacoustic signal detection system of this embodiment. The optical system comprises an exciting-light optical system 310, an interference optical system 320, and a signal processing system 330. The optical system uses a NOSM as a specimen exciting means and an interference optical system comprising a NOSM as a means for detecting a minute displacement of the specimen surface caused by the photoacoustic effect.

The exciting-light optical system 310 modulates the intensity of parallel light irradiated from a laser 31 at a predetermined frequency by an acoustic-optical modulation element 32, enlarges the intermittent light to a desired beam diameter by a beam expander 33, allows it to reflect off of a dichroic mirror 80, focuses it by a lens 35, and sends it to a NOSM tip 36c. The NOSM tip type is required to be the one shown in FIG. 18(c). The gap between the aperture 105 of the NOSM tip 36a and the specimen 7 is close to the size of the aperture. The light, which passes through the aperture 105 of the NOSM tip 36a, forms a minute optical spot of about 10 nm on the surface 104 of the specimen 7.

This minute optical spot generates elastic heat waves (ultrasonic waves) in the specimen on the basis of the photoacoustic effect and a minute displacement on the surface of the specimen 7 simultaneously. In this embodiment, this minute displacement is detected by a heterodyne Mach-Zehnder interferometer system comprising a NOSM which is described later.

The interference optical system 320 decomposes parallel light irradiated from a laser 91, which is different in wave length from the laser 31, to zeroth-order diffracted light and first-order diffracted light by an acoustic-optical modulation element 92. The first-order diffracted light is shifted in frequency by the drive frequency $f_B$ of the acoustic-optical modulation element. The zeroth-order diffracted light reflects off of mirrors 93 and 94, is enlarged to a desired beam diameter by a beam expander 95, reflects off of a beam splitter 96, passes through the dichroic mirror 80, is focused by the lens 35, and sent to the NOSM tip 36a. In the same way as with the exciting-light optical system 310, the light, which passes through the aperture 105 of the NOSM tip 36a, forms a minute optical spot of about 10 nm on the surface 104 of the specimen 7. The reflected light passes through the aperture 105 of the NOSM tip 36a once again and is changed to parallel light by the lens 35. The reflected light contains the minute displacement of the surface of the specimen 7 on the basis of the photoacoustic effect as phase information. The reflected light, which is changed to parallel light by the lens 35, passes through the dichroic mirror 80 and the beam splitters 96 and 99.

The first-order diffractive light irradiated from the acousto-optical modulation element 92 reflects off of the mirrors 93 and 97, is enlarged to a desired beam diameter by a beam expander 98, reflects off of the beam splitter 99, and interferes with the reflected light from the specimen 7 simultaneously. This interfered light contains phase information corresponding to the minute displacement generated on the surface of the specimen 7, focuses to a back focal point 115 by a lens 100, and is detected by a photoelectric conversion element 102 such as a photodiode. A pin hole 101 is installed at the back focal point 115 in the same way as with the third embodiment so as to shield stray light or interference components generated in the lens 35 or 100 or in the NOSM tip 36a, interference components generated in the transparent thin film on the specimen, or high-order diffracted light components generated by minute irregularities of the specimen surface.

Assuming that the output of the laser 91 is 1, the interference intensity signal $I_D$, which is photoelectrically converted, is expressed by Equation (4).

$$I_D = I_R + I_S + 2\sqrt{I_R}\sqrt{I_S} \cdot \cos\{2\pi f_B t - 4\pi\delta(t)/\lambda + \phi(t)\} \quad (4)$$

where $\delta(t) = A\cos(2\pi f_L t)$.

A symbol $I_R$ indicates intensity of the first-order diffractive light which reflects off of the beam splitter 99, $I_S$ intensity of the zeroth-order diffractive light which reflects off of the specimen 7 and passes through the beam splitter 99, $f_B$ a modulation frequency of the acoustic-optical modulation element 92, $\delta(t)$ a minute displacement of the surface of the specimen 7, A an intrinsic constant of the specimen material, $f_L$ a modulation frequency of the laser 31, $\phi(t)$ a phase on the basis of the optical path difference in the interferometer, and $\lambda$ an oscillation wave length of the laser 91. This interference intensity signal $I_D$ is subjected to phase-amplitude conversion by a phase detection circuit 103, and a signal in proportion to $\delta(t)$ is outputted. In this embodiment, a signal switching unit 42 is connected to a terminal A as shown in FIG. 24. The output signal from the phase detection circuit 103 is sent to a lock-in amplifier 43 of the signal processing system 330. In the lock-in amplifier 43, the amplitude of the modulation frequency component contained in the interference signal and the phase component for a modulation signal from an oscillator 40, which is used for driving an acousto-optical modulation element 32, are extracted using the modulation signal as a reference signal. The frequency and phase component have information on a thermal diffusion area Vth which is determined by the modulation frequency. When a defect such as a crack or a minute portion with a different thermal impedance exists in the thermal diffusion area Vth 23, the frequency and phase of the modulation frequency component of the reflected light detection signal are changed so as to indicate the presence of such a defect or minute portion.

This interference signal is sent to a comparator 46 simultaneously. The comparator 46 compares a reference signal sent from a CPU 44 with the detected interference light signal so as to keep the distance between the NOSM tip 36a and the specimen 7 constant, and sends the differential signal to a high-voltage amplifier 48 for driving the piezoelectric element 39 via a low-pass filter 47. The frequency characteristics of the low-pass filter 47 are as shown in FIG. 19 in the same way as with the first embodiment. The low-pass filter does not follow a change in the reflected light signal (this change corresponds to a change in the modulation frequency $f_L$) corresponding to a minute displacement of the surface of the specimen 7 caused by the photoacoustic effect, but follows changes in the distance between the NOSM tip 36a and the specimen 7 caused by irregularities of the specimen surface or thermal drifting for a comparatively long period of time during scanning of the specimen 7, sends a control signal for driving the piezoelectric element 39 to the high-voltage amplifier 48, and moves the NOSM tip 36a. As a result, the distance between the NOSM tip 36a and the specimen 7 can be kept constant always regardless of irregularities of the surface of the specimen 7 as shown in FIG. 20 in the same way as with the first embodiment, a minute optical spot with a fixed diameter can be formed always on the specimen without being affected by irregularities of the specimen surface, and a photoacoustic signal can be stably detected always. The configurations and functions of the XY stage 49 and Z stage 50 are the same as those of the first embodiment.

A position signal from the XY stage 49 and an output signal from the lock-in amplifier 43 are processed by the CPU 44, and a photoacoustic signal at each point on the specimen 7 or a two-dimensional photoacoustic image is outputted to a display 45 such as a monitor TV.

In this embodiment, as described above, a minute optical spot of about 10 nm is formed on the specimen surface by the NOSM and a minute displacement of the specimen surface on the basis of the photoacoustic effect in the specimen caused by this minute optical spot is detected as a change in the interference signal of the interference optical system comprising the NOSM tip. In this embodiment, the specimen surface can be excited by a minute optical spot of about 10 nm because the NOSM is used as a specimen exciting means and the resolution of a photoacoustic signal in the transverse direction is extremely improved. Furthermore, by using the heterodyne interference optical system comprising the NOSM tip for detecting the photoacoustic effect, the detection sensitivity is extremely improved. The detected interference signal can be used as a control signal for the distance between the NOSM tip and specimen for a comparatively long period of time via the comparator and the low-pass filter. Therefore, a photoacoustic signal can be detected stably for an uneven specimen.

Furthermore in this embodiment, even when there is a reflectivity distribution provided on the specimen surface, a photoacoustic signal can be detected stably without being affected.

The sixth embodiment of a photoacoustic signal detection apparatus whereto the present invention is applied will be described with reference to FIG. 24. In this embodiment, the configuration of the photoacoustic signal detection system is the same as that of the fifth embodiment shown in FIG. 24. Therefore, it will not be described hereunder. In this embodiment, the signal switching unit 42 is connected to the terminal B. In FIG. 24, the detected reflected light signal is sent to the comparator 46, and a control signal for keeping the interference light constant or for keeping the distance between the NOSM tip 36a and the specimen constant is sent to the lock-in amplifier 43 and simultaneously to the high-voltage amplifier 48 for driving the piezoelectric element 39 via the low-pass filter 47. In this embodiment, this control signal is used as a signal for detecting a minute displacement of the surface of the specimen 7 caused by the photoacoustic effect. The modulation frequency $f_L$ of the laser 31 is required to be set to a value so that the piezoelectric element 39 can be controlled as shown in FIG. 21 in the same way as with the second embodiment. The processing of the lock-in amplifier 43 and subsequent units is the same as that of the fifth embodiment, and finally a two-dimensional photoacoustic image is outputted to the display 45 such as a monitor TV.

This embodiment can obtain good results equal to those of the fifth embodiment though the modulation frequency is limited to an extent.

According to the present invention, since an exciting means of a photoacoustic signal detection apparatus comprises a near-field optical scanning microscope (NOSM), the photoacoustic effect can be generated in a local area of 10 to 100 nm and the resolution of a photoacoustic signal in the transverse direction can be extremely improved.

According to the present invention, since an exciting means comprises a near-field optical scanning microscope and a means for detecting the photoacoustic effect comprises a scanning tunneling microscope, a near-field optical scanning microscope, or a photo-interferometer using a near-field optical scanning microscope, the resolution of of a photoacoustic signal in the transverse direction and the detection sensitivity can be extremely improved, they can be applied to a specimen with an uneven surface, and information of the surface and interior of a specimen can be measured with high accuracy.

What is claimed is:

1. A method for processing a minute portion comprising the steps of:
   detecting a minute portion on an element or substrate of an electron device by a near-field optical scanning microscope; and
   subjecting the detected minute portion to at least one of processing, film forming and annealing by a scanning tunneling microscope.

2. A method according to claim 1, wherein the step of detecting a near-field optical scanning microscope includes utilizing a near-field optical scanning microscope tip having a glass portion with a metal thin film coated thereon and a transparent conductive layer formed on the metal thin film 3. A method according to claim 2, wherein the transparent conductive layer of the near-field optical scanning microscope tip has a refractive index substantially equal to a medium disposed between the near-field optical scanning microscope tip and the element or substrate of the electron device.

4. A method according to claim 1, wherein the steps of detecting and subjecting includes positioning the element or substrate with respect to the near-field optical scanning microscope for detecting a minute portion thereof, moving one of the element or substrate of the electron device and the near-field optical scanning microscope and the scanning tunnelling microscope with respect to one another so that the scanning tunnelling microscope and element or substrate of the electron device are positioned for subjecting the minute portion to at least one of processing, film forming and annealing by the scanning tunnelling microscope.

5. A method according to claim 4, wherein the step of moving includes utilizing a tilting mechanism which maintains a predetermined relation of the near-field optical scanning microscope to the element or substrate of the electron device upon movement of the element or substrate of the electron device and scanning tunnelling microscope with respect to one another.

6. A method according to claim 1, wherein the electron device is a memory device and the step of subjecting includes one of removal and addition of an atom from or to the minute portion of the element or substrate of the memory device.

7. A method according to claim 6, wherein the element of the memory device is a Langumuir-Blodgett's film formed on a substrate.

8. A method for processing a minute portion comprising the steps of:
   detecting roughly an element or substrate of an electron device by a scanning electron microscope;

detecting a minute portion on the element or substrate of the electron device by a near-field optical scanning microscope; and subjecting the detected minute portion to at least one of processing, film forming and annealing by a scanning tunneling microscope.

9. A method according to claim 8, wherein the electron device is a memory device and the step of subjecting includes one of removal and addition of an atom from or to the minute portion of the element or substrate of the memory device.

10. A method according to claim 9, wherein the element of the memory device is a Langumuir-Blodgett's film formed on a substrate.

11. A method for processing a minute portion comprising the steps of:
detecting a minute portion on an element or substrate of an electron device by a scanning tunneling microscope; and
subjecting the detected minute portion to at least one of processing, film forming and annealing by a near-field optical scanning microscope.

12. A method according to claim 11, wherein the electron device is a memory device and the step of subjecting includes one of removal and addition of an atom from or to the minute portion of the element or substrate of the memory device.

13. A method according to claim 12, wherein the element of the memory device is a Langumuir-Blodgett's film formed on a substrate.

14. A method for processing a minute portion comprising the steps of:
detecting roughly an element or substrate of an electron device by a scanning electron microscope;
detecting a minute portion on the element or substrate of the electron device by a scanning tunneling microscope; and
subjecting the detected minute portion to at least one of processing, film forming and annealing by a near-field optical scanning microscope.

15. A method according to claim 14, wherein the electron device is a memory device and the step of subjecting includes one of removal and addition of an atom from or to the minute portion of the element or substrate of the memory device.

16. A method according to claim 15, wherein the element of the memory device is a Langumuir-Blodgett's film formed on a substrate.

17. A method for processing a minute portion comprising the steps of:
detecting a minute portion on an element or substrate of an electron device by a near-field optical scanning microscope; and
subjecting the detected minute portion to at least one of sputtering, CVD film forming and ion beam implantation by a focused ion beam-processing system.

18. A method for processing a minute portion comprising the steps of:
detecting roughly an element or substrate of an electron device by a scanning electron microscope;
detecting a minute portion on the element or substrate of the electron device by a near-field optical scanning microscope; and
subjecting the detected minute portion to at least one of sputtering, CVD film forming and ion beam implantation by a focused ion beam-processing system.

19. A method for analyzing a minute portion comprising the steps of:
detecting a minute portion on an element or substrate of an electron device by a near-field optical scanning microscope; and
analyzing the detected minute portion by a scanning tunneling microscope or a scanning tunneling analyzer.

20. A method for analyzing a minute portion comprising the steps of:
detecting roughly an element or substrate of an electron device by a scanning electron microscope;
detecting a minute portion on the element or substrate of the electron device by a near-field optical scanning microscope; and
analyzing the detected minute portion by a scanning tunneling microscope or a scanning tunneling analyzer.

21. A method for analyzing a minute portion comprising the steps of:
detecting a minute portion on an element or substrate of an electron device by a scanning tunneling microscope; and
analyzing the detected minute portion by a near-field optical scanning microscope.

22. A method for analyzing a minute portion comprising the steps of:
detecting roughly an element or substrate of an electron device by a scanning electron microscope;
detecting a minute portion on the element or substrate of the electron device by a scanning tunneling microscope; and
analyzing the detected minute portion by a near-field optical scanning microscope.

23. An apparatus or processing a minute portion comprising:
a near-field optical scanning microscope for detecting a minute portion on an element or substrate of an electron device; and
a scanning tunneling microscope for subjecting the detected minute portion to at least one of processing, film forming and annealing on the basis of the information on the minute portion detected by said near-field optical scanning microscope.

24. An apparatus according to claim 23, wherein the near-field optical scanning microscope includes a near-field optical scanning microscope tip having a glass portion with a metal thin film coated thereon and a transparent conductive layer formed on the metal thin film.

25. An apparatus according to claim 24, wherein the transparent conductive layer of the near-field optical scanning microscope tip has a refractive index substantially equal to a medium disposed between the near-field optical scanning microscope tip and the element or substrate of the electron device.

26. An apparatus according to claim 23, further comprising means for positioning the element or substrate of the electron device with respect to the near-field optical scanning microscope for detecting a minute portion thereof, and means for moving one of the element or substrate of the electron device and the near-field optical scanning microscope and the scanning tunnelling microscope with respect to one another so that the scanning tunnelling microscope and element or substrate of the electron device are positioned for subjecting the minute portion to at least one of processing, film forming and annealing by the scanning tunnelling microscope.

27. An apparatus according to claim 26, wherein the moving means includes a tilting mechanism which a predetermined relation of the near-field optical scanning microscope to the element or substrate of the electron device upon movement of the element or substrate of the electron device and scanning tunnelling microscope with respect to one another.

28. An apparatus according to claim 23, wherein said apparatus further comprises a vacuum chamber in which the element or substrate of the electron device is disposed, and the respective principal parts of said near-field optical scanning microscope and said scanning tunneling microscope are installed in said vacuum chamber.

29. An apparatus according to claim 28, wherein said vacuum chamber has a processing gas inlet.

30. An apparatus according to claim 28, wherein said apparatus further comprises a specimen table with a driving unit disposed in said vacuum chamber.

31. An apparatus according to claim 23, wherein said apparatus further comprises:
a vacuum chamber with a gas exhausting unit and a processing gas inlet;
a specimen table in said vacuum chamber for mounting the element or substrate of the electron device;
a driving unit for driving said specimen table in X, Y and Z directions by rough and minute steps; and
a scanning electron microscope for roughly detecting a portion of the element or substrate of the electron device, and
wherein said near-field optical scanning microscope detects the minute portion on the element or substrate of the electron device on the basis of the rough information on the portion detected by said scanning electron microscope.

32. An apparatus according to claim 23, wherein said apparatus further comprises means for rotating at least one of tips of said near-field optical scanning microscope and said scanning tunneling microscope round an end point of said at least one of tips.

33. An apparatus for processing a minute portion comprising:
a scanning electron microscope for roughly detecting an element or substrate of an electron device;
a near-field optical scanning microscope for detecting a minute portion on the element or substrate of the electron device on the basis of the rough information detected by said scanning electron microscope; and
a scanning tunneling microscope for subjecting the detected minute portion to at least one of processing, film forming and annealing on the basis of the information on the minute portion detected by said near-field optical scanning microscope.

34. An apparatus for processing a minute portion comprising:
a scanning tunneling microscope for detecting a minute portion on an element or substrate of an electron device; and
a near-field optical scanning microscope for subjecting the detected minute portion to at least one of processing, film forming and annealing on the basis of the information on the minute portion detected by said scanning tunneling microscope.

35. An apparatus according to claim 34, wherein said apparatus further comprises means for rotating at least one of tips of said scanning tunneling microscope and said near-field optical scanning microscope round an end point of said at least one of tips.

36. An apparatus for processing a minute portion comprising:
a scanning electron microscope for roughly detecting an element or substrate of an electron device;
a scanning tunneling microscope for detecting a minute portion on the element or substrate of the electron device on the basis of the rough information detected by said scanning electron microscope; and
a near-field optical scanning microscope for subjecting the detected minute portion to at least one of processing, film forming and annealing on the basis of the information on the minute portion detected by said scanning tunneling microscope.

37. An apparatus for processing a minute portion comprising:
a near-field optical scanning microscope for detecting a minute portion on an element or substrate of an electron device; and
a focused ion beam-processing system for subjecting the detected minute portion to at least one of sputtering, CVD film forming and ion beam implantation on he basis of the information on the minute portion detected by said near-field optical scanning microscope.

38. An apparatus for processing a minute portion comprising:
a scanning electron microscope for roughly detecting an element or substrate of an electron device;
a near-field optical scanning microscope for detecting a minute portion on the element or substrate of the electron device on the basis of the rough information detected by said scanning electron microscope; and
a focused ion beam-processing system for subjecting the detected minute portion to at least one of sputtering, CVD film forming and ion beam implantation on the basis of the information on the minute portion detected by said near-field optical scanning microscope.

39. An apparatus according to claim 38, wherein said apparatus further comprises a vacuum chamber in which the element or substrate of the electron device is disposed, and the respective principal parts of said scanning electron microscope, said near-field optical scanning microscope and said focused ion beam-processing system are installed in said vacuum chamber.

40. An apparatus according to claim 39, wherein said apparatus further comprises means for rotating a tip of said near-field optical scanning microscope round an end point of said tip.

41. An apparatus for analyzing a minute portion comprising:
a near-field optical scanning microscope for detecting a minute portion on an element or substrate of an electron device; and
a scanning tunneling microscope or a scanning tunneling analyzer for analyzing the detected minute portion on the basis of the information on the minute portion detected by said near-field optical scanning microscope.

42. An apparatus for analyzing a minute portion comprising:
a scanning electron microscope for roughly detecting an element or substrate of an electron device;

a near-field optical scanning microscope for detecting a minute portion on the element or substrate of the electron device on the basis of the rough information detected by said scanning electron microscope; and a scanning tunneling microscope or a scanning tunneling analyzer for analyzing the detected minute portion on the basis of the information on the minute portion detected by said near-field optical scanning microscope.

43. An apparatus for analyzing a minute portion comprising:

a scanning tunneling microscope for detecting a minute portion on an element or substrate of an electron device; and a near-field optical scanning microscope for analyzing the detected minute portion on the basis of the information on the minute portion detected by said scanning tunneling microscope.

44. An apparatus for analyzing a minute portion according to claim 43 wherein light for the above near-field optical scanning microscope is a laser beam with a wide wave length band.

45. An apparatus for analyzing a minute portion according to claim 43 wherein light for the above near-field optical scanning microscope is a dye laser beam.

46. An apparatus for analyzing a minute portion comprising:

a scanning electron microscope for roughly detecting an element or substrate of an electron device;

a scanning tunneling microscope for detecting a minute portion on the element or substrate of the electron device on the basis of the rough information detected by said scanning electron microscope; and a near-field optical scanning microscope for analyzing the detected minute portion on the basis of the information on the minute portion detected by said scanning tunneling microscope.

47. A method for processing a minute portion comprising the steps of:

detecting the minute portion of an element or substrate of an electron device by a near-field optical scanning microscope; and subjecting the detected minute portion to at least one of processing, film forming and annealing by the near-field optical scanning microscope.

48. A method according to claim 47, wherein the steps of detecting and subjecting include utilizing a near-field optical scanning microscope tip having a glass portion with a metal thin film coated thereon and a transparent conductive layer formed on the metal thin film.

49. A method according to claim 48, wherein the transparent conductive layer of the near-field optical scanning microscope tip has a refractive index substantially equal to that of a medium disposed between the near-field optical scanning microscope tip and the element or substrate of the electron device.

50. A method for processing a minute portion comprising the steps of:

detecting roughly an element or substrate of an electron device by a scanning electron microscope;

detecting a minute portion of the element or substrate of the electron device by a near-field optical scanning microscope; and subjecting the detected minute portion to at least one of processing, film forming and annealing by the near-field optical scanning microscope.

51. A method according to claim 50, wherein the steps of detecting and subjecting include utilizing a near-field optical scanning microscope tip having a glass portion with a metal thin film coated thereon and a transparent conductive layer formed on the metal thin film.

52. A method according to claim 51, wherein the transparent conductive layer of the near-field optical scanning microscope tip has a refractive index substantially equal to that of a medium disposed between the near-field optical scanning microscope tip and the element or substrate of the electron device.

53. A method for processing a minute portion comprising the steps of:

roughly detecting a portion of an element or substrate of an electron device and a tip of a near-field optical scanning microscope by a scanning electron microscope;

correcting a position displacement between the detected portion of the element of substrate of the electron device and the detected tip of the near-field optical scanning microscope in a view of the scanning electron microscope;

detecting a minute portion of the element or substrate of the electron device by a near-field optical scanning microscope on the basis of the rough information detected by the scanning electron microscope; and adjusting a precise position of the detected minute portion of the element or substrate of the electron device in a view of the near-field optical scanning microscope.

54. A method according to claim 53, wherein the tip of the near-field optical scanning microscope has a glass portion with a metal thin film coated thereon and a transparent conductive layer formed on the metal thin film.

55. A method according to claim 54, wherein the transparent conductive layer of the near-field optical scanning microscope tip has a refractive index substantially equal to that of a medium disposed between the near-field optical scanning microscope tip and the element or substrate of the electron.

56. A method for processing a minute portion comprising the steps of:

roughly detecting a portion of an element or substrate of an electron device and a tip of a near-field optical scanning microscope by a scanning electron microscope;

correcting a position displacement between the detected portion of the element or substrate of the electron device and the detected tip of the near-field optical scanning microscope in a view of the scanning electron microscope;

detecting a minute portion of the element or substrate of the electron device by the near-field optical scanning microscope on the basis of the rough information on the portion detected by the scanning electron microscope;

adjusting a precise position of the detected minute portion of the element or substrate of the electron device in a view of the near-field optical scanning microscope; and subjecting the position-adjusted minute portion of the element or substrate of the electron device to at least one of processing, film forming and annealing by one of the near-field optical scanning microscope and a scanning tunneling microscope.

57. A method according to claim 56, wherein the tip of the near-field optical scanning microscope has a glass portion with a metal thin film coated thereon and a transparent conductive layer formed on the metal thin film.

58. A method according to claim 57, wherein the tip of the near-field optical scanning microscope further has a tip for the scanning tunneling microscope.

59. A method according to claim 58, wherein the tip for the scanning tunneling microscope is arranged on a center axis of the tip of the near-field optical scanning microscope.

60. A method according to claim 59, wherein the transparent conductive layer of the near-field optical scanning microscope tip has a refractive index substantially equal to that of a medium disposed between the near-field optical scanning microscope tip and the element or substrate of the electron device.

61. A method according to claim 57, wherein the transparent conductive layer of the near-field optical scanning microscope tip has a refractive index substantially equal to that of a medium disposed between the near-field optical scanning microscope tip and the element or substrate of the electron device.

62. A method according to claim 58, wherein the transparent conductive layer of the near-field optical scanning microscope tip has a refractive index substantially equal to that of a medium disposed between the near-field optical scanning microscope tip and the element or substrate of the electron device.

63. A near-field optical scanning microscope comprising:
a near-field optical microscope tip;
a supporting mechanism for rotatably supporting said tip, said supporting mechanism having a rotation axis located at the same level as a surface of a specimen; and
an optical system for guiding light to said tip, said optical system being supported by said supporting mechanism,
wherein the light is introduced into said optical system along the rotation axis of said mechanism.

64. A tip for a near-field optical scanning microscope comprising:
a glass tip;
a metal thin film coated on said glass tip; and
a transparent conductive layer formed on said metal thin film.

65. A tip according to claim 64, wherein a protrusion for flowing a tunnel current is formed on said transparent conductive layer.

66. A tip according to claim 65, wherein said protrusion is formed on a center axis of the tip.

67. A tip according to claim 66, wherein a refractive index of said transparent conductive layer is substantially equal to that of a medium disposed between the tip and a specimen.

68. A tip according to claim 65, wherein a refractive index of said transparent conductive layer is substantially equal to that of a medium disposed between the tip and a specimen.

69. A tip according to claim 64, wherein a refractive index of said transparent conductive layer is substantially equal to that of a medium disposed between the tip and a specimen.

* * * * *